US010933121B2

(12) United States Patent
Poulsen et al.

(10) Patent No.: US 10,933,121 B2
(45) Date of Patent: Mar. 2, 2021

(54) GLYCOSIDE HYDROLASES AND THEIR USE IN PREVENTING AND/OR TREATING A PATHOGENIC INFECTION IN AN ANIMAL

(71) Applicant: DUPONT NUTRITION BIOSCIENCES APS, Copenhagen (DK)

(72) Inventors: Charlotte Horsmans Poulsen, Brabrand (DK); Svend Haaning, Galten (DK)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 130 days.

(21) Appl. No.: 15/755,711

(22) PCT Filed: Aug. 30, 2016

(86) PCT No.: PCT/US2016/049439
§ 371 (c)(1),
(2) Date: Feb. 27, 2018

(87) PCT Pub. No.: WO2017/040499
PCT Pub. Date: Mar. 9, 2017

(65) Prior Publication Data
US 2019/0022193 A1    Jan. 24, 2019

Related U.S. Application Data

(60) Provisional application No. 62/213,564, filed on Sep. 2, 2015.

(51) Int. Cl.
*A61K 38/47* (2006.01)
*A23K 20/189* (2016.01)
*A23K 50/30* (2016.01)
*A61P 31/00* (2006.01)

(52) U.S. Cl.
CPC ............ *A61K 38/47* (2013.01); *A23K 20/189* (2016.05); *A23K 50/30* (2016.05); *A61P 31/00* (2018.01); *C12Y 302/01051* (2013.01)

(58) Field of Classification Search
CPC ...................................................... A61P 31/00
See application file for complete search history.

(56) References Cited

U.S. PATENT DOCUMENTS

| 5,433,946 A | 7/1995 | Allen, Jr. |
| 2004/0126370 A1 | 7/2004 | Azzo |

FOREIGN PATENT DOCUMENTS

| RU | 2173556 | 9/2001 | |
| WO | 94/25061 A1 | 11/1994 | |
| WO | WO-9425061 A1 * | 11/1994 | ........... A61K 38/465 |
| WO | 03/057138 A2 | 7/2003 | |

OTHER PUBLICATIONS

Becerra et al., Appl Microbio Biotechnol., 2015, 99:7165-7176.*
Nagy and Fekete (1999) Vet Res. 30:259-84.
Vogeli et al. (1996) Anim Genet. 27(5): 321-8).
Francis DH (2002) J Swine Health Prod. 10(4):171-5.
Meijerink et al. (1997) Mammalian Genome 8:736-41.
Torres-Pinedo and Mahmood (2004) Biochem Biophys Res Commun 125:546-53.
Ruggiero-Lopez et al. (1991) Biochem J 279:801-6.
Smith, D. W., ed. Biocomputing: Informatics and Genome Projects Academic Press, NY (1993) Book Not Included.
Griffin, A. M., and Griffin, H. G., eds. Computer Analysis of Sequence Data, Part I Humana Press, NJ (1994) Book Not Provided.
Alschul_1997_Nueleic Acids Res Set 1; 25(17):3389-402).
Sambrook et al., Molecular Cloning, Cold Spring Harbor Laborators, Press (1989).
Brigidi, DeRossi, Bertarini, Riccardi and Matteuzzi, (1990) FEMS Microbiol. Lett. 55: 135-138).
Berko, et al., (1991) in Applications of Enzyme Biotechnology, Eds. Kelly and Baldwin, Plenum Press (NY):.
De Groot et al., (1998) *Nat. Blotechnol.* 16:839-842.
Nevalainen et al., "The Molecular Biology of Tricholerma and its Application to the Expression of Both Homologous and Heterologous Genes", in Molecular Industrial Mycology, Eds. Leong and Berka, Marcel Dekker Inc., NY (1992) pp. 129-148).
Kieser, T, M J. Bibb, M J. Buttner, K F Chater, and D. A. Hopwood (2000).
Ausubel, F. M. et. al., *Short Protocols in Molecular Biology*, 5th Ed. Current Protocols and John Wiley and Sons, Inc., N.Y.,(2002)—Book.
Hedegaard C J, Strobe M L, Hansen M B, Lindved B K, Lihme A, Boye M, et al. (2016). Natural Pig Plasma Immunoglobulins Have Anti-Bacterial Effects: Potential for Use as Feed Supplement for Treatment of Intestinal Infections in Pigs. PLoS One 11(1): e0147373.
Daniela Chessa et al: "*Salmonella enterica* serotype Typhimurium Std fimbriae bind terminal [alpha] (1,2) fucose residues in the cecal mucosa", Molecular Microbiology., vol. 71, No. 4 Feb. 2009 (2009-01) pp. 864-875, XP5227127.
Marionneau S. et al., Norwaok virus binds to histo-blood goup antigens present on gastroduondenal epithelial cells of secretor individuals, Gastroenterology, 2002, Vo. 122, No. 7 pp. 1967-1977.
Fernandez-Abolos (2003) Microbiol 149:1623-4632.

(Continued)

*Primary Examiner* — Bin Shen
(74) *Attorney, Agent, or Firm* — Matthew Duane Show

(57) ABSTRACT

Disclosed are methods and compositions using glycoside hydrolases, such as an alpha-L-fucosidases, to prevent and/or treat a pathogenic infection and/or diarrhea in an animal wherein the pathogenic infection is caused by a pathogen capable of binding to an animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site.

15 Claims, 13 Drawing Sheets

(56) References Cited

OTHER PUBLICATIONS

Biol et al. (1987) Pediatr Res 22:250-6.
Jones et al., (1985) EMBO J 4:2411-2418.
De Almeida et al., (1989) Mol Gen Genetics 218:78-86.
Lesk, A. M., ed., Computational Molecular Biology Oxford University Press, NY (1988).
Smith, D. W., ed. Biocomputing: Informatics and Genome Projects Academic Press, NY (1993) Book Not Included—Cite Only.
Griffin, A. M., and Griffin, H. G., eds. Computer Analysis of Sequence Data, Part I Humana Press, NJ (1994) Book Not Provided Cite Only.
Von Heinje, G., ed., Sequence Analysis in Molecular Biology Academic Press (1987).
Emboss Open Software Suite (EMBL-EBI; Rice et al., Trends in Genetics 16, (6):276-277 (2000).
Higgins and Sharp, CABIOS, 5:151-153 (1989).
Chenna et al., Nucleic Acids Res 31 (13):3497-500 (2003).
Alschul_1997_Nucleic Acids Res Set 1; 25(17):3389-402).
Sambrook et al., Molecular Cloning, Cold Spring Harbor Laboratory Press (1989).
Bennett and Lasure (Eds.) More Gene Manipulations in Fungi, Academic Press. 396-428 (1991).
Nunberg, et al., (1984) Mol. Cell Biol. 4:2306-2315.
Finkelstein in Biotechnology of Filamentous Fungi, Finkelstein et al. Eds. Butterworth-Heinemann, Boston, Mass. (1992), Chap. 6.
Kinghorn et al. (1992) Applied Molecular Genetics of Filamentous Fungi, Blackie Academic and Professional, Chapman and Hall, London.
Penttila et al., (1987) Gene 61: 155-164.
Lorito, Hayes, DiPietro and Harman, (1993) Curr. Genet. 24: 349-356.
Goldman, VanMontagu and Herrera-Estrella, (1990) Curr. Genet. 17:169-174.
Yelton, Hamer and Timberlake, (1984) Proc. Natl. Acad. Sci. USA 81: 1470-1474.
Bajar, Podila and Kolattukudy, (1991) Proc. Natl. Acad. Sci. USA 88: 8202-8212.
Hopwood et al., 1985, Genetic Manipulation of *Streptomyces*: Laboratory Manual, The John Innes Foundation, Norwich, UK.
Brigidi, DeRossi, Bertarini, Riccardi and Matteuzzi, (1990) FEMS Microthol. Lett. 55: 135-138).
Berka et al., (1991) in Applications of Enzyme Biotechnology, Eds. Kelly and Baldwin, Plenum Press (NY).
Cao et al., (2000) Sci. 9:991-1001.
Campbell et al., (1989) Curro Genet. 16:53-56.

De Groot et al., (1998) Nat. Biotechnol 16:839-842.
Harkki et ale (1991); Enzyme Microb. Technol. 13:227-233.
Harkki et al., (1989) Bio Technol. 7:596-603.
Nevalainen et al., "The Molecular Biology of Trichoderma and its Application to the Expression of Both Homologous and Heterologous Genes", in Molecular Industrial Mycology, Eds. Leong and Berko, Marcel Dekker Inc., NY (1992) pp. 129-148).
Ilmen et al 1997 ("Regulation of cellulose gene expression in the filamentous fungus *Trichoderma reesei*." Appl. Envir. Microbiol. 63:1298-1306).
Kieser, T, M J. Bibb, M J. Buttner. K F Chafer, and D. A. Hopwood (2000).
Harwood, et al., (1990) Molecular Biological Methods for *B* Acillus, John Wiley and/or from the American Type Culture, Collection (ATCC; www.atcc.org).
Cao et al. J Biol Chem (2014) 289(37):25624-3853.
Singleton, et al., Dictionary of Microbiology and Molecular Biology, 2D ED., John Wiley and Sons, New York (1994).
Hale & Marham, The Harper Collins Dictionary of Biology, Harper Perennial, N.Y. (1991).
Sambrook, J. and Russell, D., Molecular Cloning: A Laboratory Manual, Third Edition, Cold Spring Harbor Laboratory Press, Cold Spring Harbor, N.Y. (2001).
Ausubel, F. M. et. al., Short Protocols in Molecular Biology, 5$^{th}$ Ed. Current Protocols and John Wiley and Sons, Inc., N.Y.,(2002)—Book (Cited Only).
Vogtentanz (2007) Protein Expr. Purif, 55:40-52.
Hedegaard C J, Strube M L, Hansen M B, Lindved B K, Lihme A, Boye M, et al. (2016). Natural Pig Plasma Immunogiobulins Have Anti-Bacterial Effects: Potential for Use as Feed Supplement for Treatment of Intestinal Infections in Pigs. PLoS One 11(1): e0147373.
Daniela Chessa et al: "Salmonella enterica serotype Typhimurium Std fimbriae bind terminal [alpha] (1,2) fucose residues in the cecal mucosa", Molecular Microbiology., vol. 71, No. 4 Feb. 2009 (Jan. 2009) pp. 864-875, XP5227127.
Marionneau S. et al., Norwaok virus binds to histo-blood goup antigens present on gastroduondenal epithelial cells of secretor individuals, Gastroenterology, 2002, vol. 122, No. 7 pp. 1967-1977.
Meijerink E. et al., A DNA polymorphism influencing alpha (1,2) fucosyltransferace activity of the pig FUT1 enzyme determines suspectibility of small intestinal epithelium to *Escherichia coli* F18 adhesion Immunogenetics, 2000, vol. 52, pp. 129-136.
Ausubel, Current Protocols in Molecular Biology, vol. 1 (1987).
Van den Hondel et al. Heterologous Gene Expression in Filamentous Fungi, TNO Medical Biology Laboratory (1991).
Kelley et al., (1985) EMBO J. 4:475-479.
Fernandez-Abolos (2003) Microbiol 149:1623-1632.

\* cited by examiner

Exemplary plasmid map p3JM

Exemplary plasmid map p2JM

Exemplary plasmid map of pGXT-GOI pH effect on fucosidase activity towards 2'-fucosyllactose. Corresponding accession numbers can be found in Table 1

Temperature effect on fucosidases activity towards 2'-fucosyllactose. Corresponding accession numbers can be found in Table 1

Fucosidases assayed in the presence and absence of pepsin at higher pH. Corresponding accession numbers can be found in Table 1.

Structures of A, B, and O Oligosaccharide Antigens
Addreviations: Fuc=L-fucose; Gal=D-galacloac; GalNAc = N-acetylgalactosamine; GlcNAc = N-acetylglucosamine

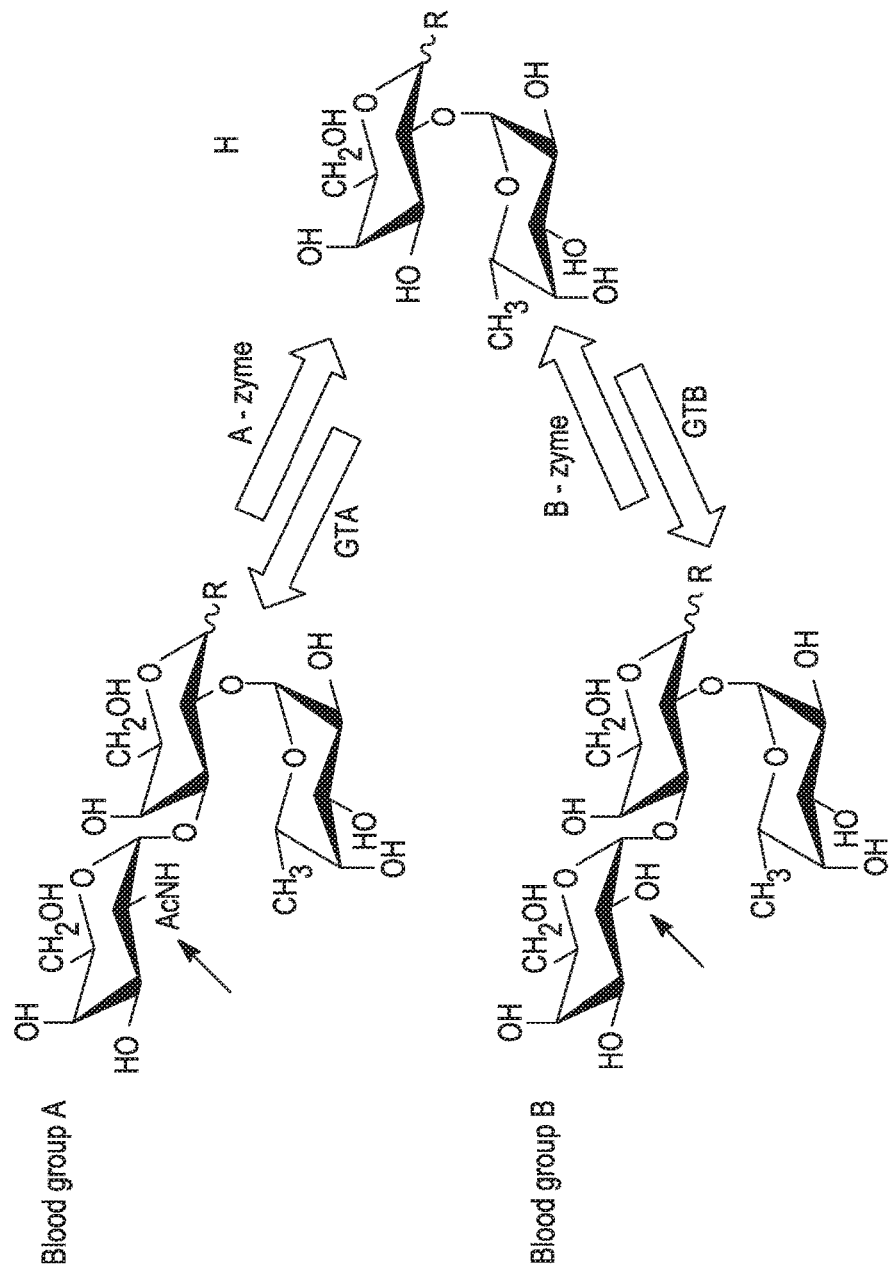

FIG. 10
Prior Art

Structural basis of the ABO blood group antigens. The black arrows indicate the different C-2 N-acetyl group of GalNAc and OH group of Gal in the A and B epitopes, respectively. These epitopes are positioned at the termini of oligosaccharide chains on glycoplipids and glycoproteins as indicated by R.
GTA= alpha1,3-N_acetylgalactosaminyltransferase
GTB =alpha-galactosyltransferase
A-zyme = alpha-N-acetylgalactosaminidase
B-zyme = alpha-galactosidase Fucosidase (CRC08392) induced release of fucose from tissue sample from the small intestine of a piglet. Corresponding accession numbers can be found in Table 1

GLYCOSIDE HYDROLASES AND THEIR USE IN PREVENTING AND/OR TREATING A PATHOGENIC INFECTION IN AN ANIMAL

CROSS-REFERENCE TO RELATED APPLICATIONS

This application is a U.S. National Stage entry under 35 U.S.C. § 371 of International Patent Application No. PCT/US2016/049439, filed Aug. 30, 2016, which in turn claims the benefit of U.S. Provisional Application No. 62/213,564, filed Sep. 2, 2015, the disclosure of each of which is incorporated herein by reference in its entirety.

FIELD

The field relates to glycoside hydrolases, such as alpha-L-fucosidases, and, in particular, their use in preventing and/or treating intestinal pathogenic infections and/or diarrhea in animals.

BACKGROUND

Use of antibiotics in treating both humans and animals has resulted in antimicrobial resistance that now has become a major global health threat. Thus, the quest is on for developing alternatives to antibiotics in order to address this global health concern.

Consumers are very concerned about the widespread use of antibiotics in animal feed. Both retailers and farmers will need to change in response to this change in consumer preference for antibiotic-free meat.

Enterotoxigenic *Escherichia (E.) coli* (ETEC) is the most common type of colibacillosis of young animals, such as pigs and calves, typically appearing as severe watery diarrhea. It is also a significant cause of diarrhea among travelers ("Traveler's Diarrhea") and children in the developing world.

Almost all ETEC bacteria are known to adhere to receptors on the small intestinal epithelium by proteinaceous surface appendages (fimbriae and pili) or by afimbrial proteins. Furthermore, they secrete protein toxins (enterotoxins) to reduce absorption and to increase fluid and electrolyte secretion of the small intestinal epithelial cells. The enterotoxins act locally on enterocytes. Details of the epidemiology, pathogenesis, diagnosis and prevention of ETEC infections and diarrhea in animals can be found in Nagy and Fekete (1999) Vet Res. 30:259-84.

More specifically, ETEC and Enterotoxaemic (ETEEC) *Escherichia coli* (F18$^+$ *E. Coli*) have been found to express F18 fimbriae that colonize the small intestine and cause diarrhea in very young animals, such as piglets and calves and is a major cause of human mortality in the third world. Protection against such diseases can be established by preventing fimbrial adhesion of such pathogens to animal intestinal cells. Thus, there is a need to find new and alternative approaches for prevention and treatment of pathogenic infections, such as ETEC.

SUMMARY

In one aspect, what is disclosed is a method of preventing and/or treating an animal from having an intestinal pathogenic infection and/or diarrhea wherein the pathogenic infection and/or diarrhea is caused by a pathogen capable of binding to animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site. In some aspects, the glycoside hydrolase is an alpha-L-fucosidase.

In another aspect, the alpha-L-fucosidase is capable of removing a terminal alpha-1,2-linked fucose group from a glycan-containing structure either alone or in combination with an enzyme capable of (a) converting a blood group A antigen to a blood group H antigen or (b) converting a blood group B antigen to blood group H antigen. More particularly, the alpha-L-fucosidase is selected from the group consisting of glycoside hydrolase family 95 (GH95) and glycoside hydrolase family 29 (GH 29).

In a third aspect, the pathogen is *Escherichia coli* expressing F18 fimbriae.

In a fourth aspect, the disclosed method further comprises administering to the animal an effective amount of an alpha-L-fucosidase in combination with at least one direct fed microbial either alone or in combination with at least one protease and, furthermore, the alpha-L-fucosidase is encapsulated.

In a fifth aspect, the disclosed method further comprises that the alpha-L-fucosidase, whether encapsulated or not encapsulated, and/or the direct fed microbial and/or the protease are administered in an animal feed or a premix. Furthermore, the alpha-L-fucosidase, whether encapsulated or not encapsulated, may be in the form of a granule for use in animal feed or a premix.

In a sixth aspect, what is disclosed is a composition for preventing and/or treating an animal having an intestinal pathogenic infection and/or diarrhea wherein the pathogenic infection and/or diarrhea is caused by a pathogen capable of binding to an animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site. In some aspects, the glycoside hydrolase is an alpha-L-fucosidase.

This alpha-L-fucosidase is capable of removing a terminal alpha-1,2-linked fucose group from a glycan-containing structure either alone or in combination with an enzyme capable (a) converting a blood group A antigen to a blood group H antigen or (b) converting a blood group B antigen to blood group H antigen. Furthermore, the alpha-L-fucosidase is selected from the group consisting of glycoside hydrolase family 95 (GH95) and glycoside hydrolase family 29 (GH 29).

In a seventh aspect, the pathogen is *Escherichia coli* expressing F18 fimbriae.

In an eighth aspect, the disclosed composition further comprises at least one direct fed microbial, either alone or in combination with at least one protease wherein the alpha-L-fucosidase may or may not be encapsulated and may be used in animal feed or a premix.

In a ninth aspect, the disclosed composition may comprise an alpha-L-fucosidase whether or not encapsulated, at least one direct fed microbial and/or at least one protease are administered to an animal as a feed or a premix and the alpha-L-fucosidase may be in the form of a granule for use in animal feed or a premix.

BRIEF DESCRIPTION OF THE DRAWINGS

FIG. 10 depicts the structural basis of the ABO blood group antigens.

DETAILED DESCRIPTION

Figure 1A:
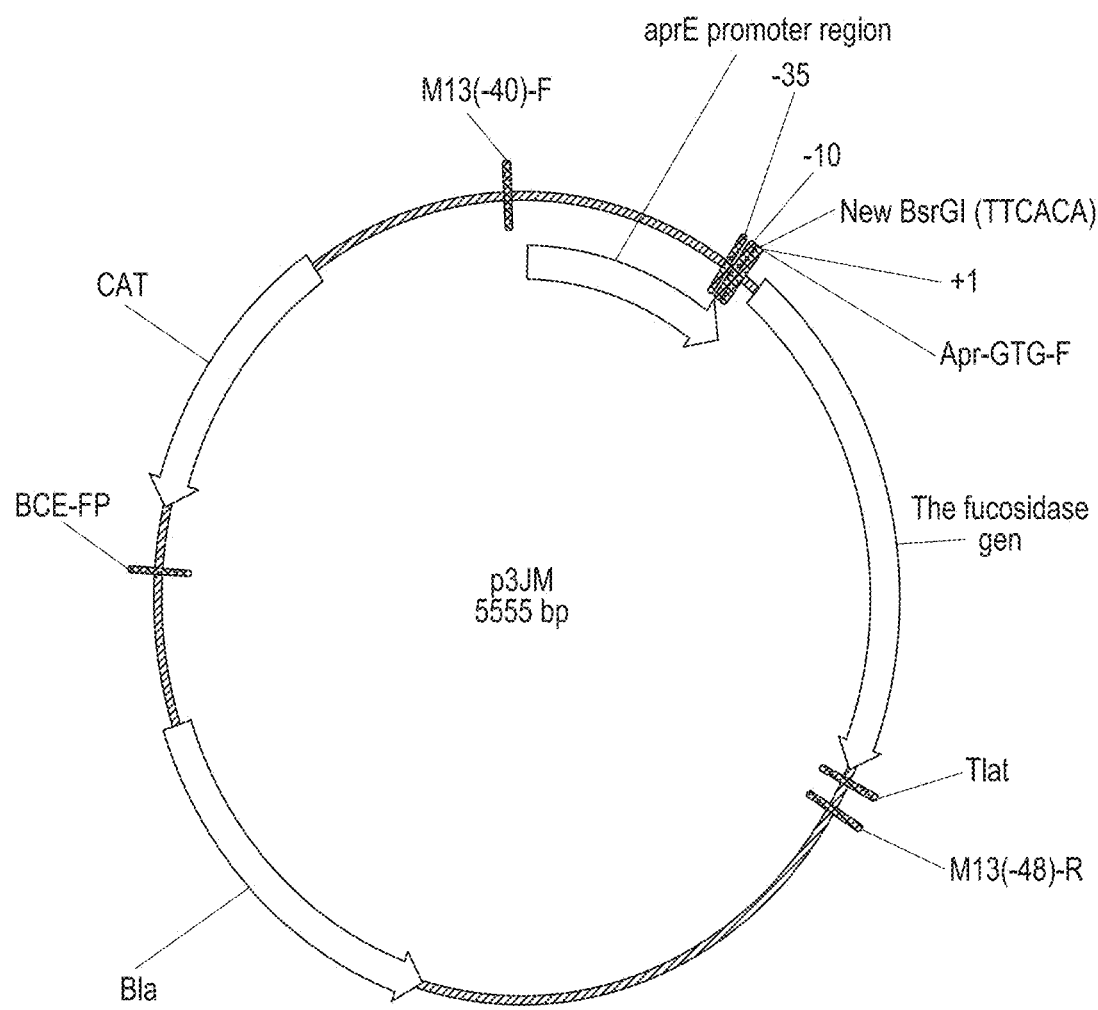
FIG. 1A depicts an exemplary plasmid map of p3JM.

All patents, patent applications, and publications cited are incorporated herein by reference in their entirety.

In this disclosure, a number of terms and abbreviations are used. The following definitions apply unless specifically stated otherwise.

The articles "a", "an", and "the" preceding an element or component are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

The term "glycoside hydrolase" is used interchangeably with "glycosidases" and "glycosyl hydrolases". Glycoside hydrolases assist in the hydrolysis of glycosidic bonds in complex sugars (polysaccharides). Together with glycosyltransferases, glycosidases form the major catalytic machinery for the synthesis and breakage of glycosidic bonds. Glycoside hydrolases are classified into EC 3.2.1 as enzymes catalyzing the hydrolysis of O- or S-glycosides. Glycoside hydrolases can also be classified according to the stereochemical outcome of the hydrolysis reaction: thus they can be classified as either retaining or inverting enzymes. Glycoside hydrolases can also be classified as exo or endo acting, dependent upon whether they act at the (usually non-reducing) end or in the middle, respectively, of an oligo/polysaccharide chain. Glycoside hydrolases may also be classified by sequence or structure based methods. They are typically named after the substrate that they act upon.

The term "glycosyltransferase" refers to an enzyme that catalyzes the formation of a glycosidic bond between monosaccharides.

The terms "alpha-L-fucosidase," "alpha-L-fucoside fucohydrolase," and "alpha-fucosidase" are used interchangeably herein and refer to an enzyme in the EC class No. 3.2.1.51 that removes an L-fucose from an alpha-L-fucoside. Alpha-L-fucosidases are exoglycosidases found in a variety of organisms and mammals. Alpha-L-fucosidases have been divided into two distinct glycoside hydrolase families: alpha-L-fucosidases that catalyze hydrolysis using a retaining mechanism belong to the well known glycoside hydrolase family 29 (GH29). Alpha-L-fucosidases that catalyze hydrolysis using an inverting mechanism belong to the glycoside hydrolase family 95 (GH95).

The terms "alpha-1,2-L-fucosidase," "Almond emulsin fucosidase II," alpha-2-L-fucopyranosyl-beta-D-galactoside fucohydrolase," and "alpha-(1->2)-L-fucosidase" are used interchangeably herein and refer to an enzyme in the EC class No. 3.2.1.63 that catalyzes the hydrolysis of non-reducing terminal L-fucose residues linked to D-galactose residues by a 1,2-alpha linkage. The terms "alpha-1,3-L-fucosidase," "Almond emulsin fucosidase I," and "alpha-3-L-fucose-N-acetylglucosaminyl-glycoprotein fucohydrolase" are used interchangeably herein and refer to an enzyme in the EC class No. 3.2.1.111 that hydrolyzes (1->3)-linkages between alpha-L-fucose and N-acetylglucosamine residues.

The terms "alpha-1,6-L-fucosidase," "alpha-L-fucosidase," and "1,6-L-fucose-N-acetyl-D-glucosaminylglycopeptide fucohydrolase" are used interchangeably herein refer to an enzyme in the EC class No. 3.2.1.127 that hydrolyzes (1->6)-linkages between alpha-L-fucose and N-acetyl-D-glucosamine residues.

The terms "defucosylate" and "defucosylating" are used interchangeably and refer to an enzyme capable of removing a fucosyl group from a glycan-containing structure.

The terms "glycan" and "polysaccharide" are used interchangeably herein. Glycan refers to a polysaccharide or oligosaccharide, or the carbohydrate section of a glycoconjugate such as a glycoprotein, a glycolipid, or a proteoglycan, even if the carbohydrate is only an oligosaccharide. Glycans may be homo- or heteropolymers of monosaccharide residues. They may be linear or branched molecules. Glycans can be found attached to proteins as in glycoproteins and proteoglycans. In general, they are found on the exterior surface of cells. O- and N-linked glycans are very common in eukaryotes but may also be found, although less commonly, in prokaryotes.

The term "glycan-containing structure" as used herein refers to any structure, such as proteins, lipids and the like to which a glycan can be attached in any manner.

The term "N-acetyl-galactosylamine-containing moiety" is a structure to which an N-acetyl-galacatosylamine is attached. Such structures include, but are not limited to, carbohydrates and the like.

The term "FUT 1" as used herein refers to alpha-1,2-fucosyltransferase 1. A fucosyltransferase is an enzyme that transfers an L-fucose sugar from a GDP-fucose donor substrate to an acceptor substrate. The acceptor substrate can be another sugar such as the transfer of a fucose to a core GlcNAc sugar as in the case of N-linked glycosylation, or to a protein as in the case of O-linked glycosylation by O-fucosyltransferase. Some of the proteins in this group are responsible for the molecular basis of the blood group antigens, surface markers on the outside of the red blood cell membrane.

The term "animal" as used herein includes all non-ruminant (including humans) and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

The term "pathogen" as used herein means any causative agent of disease. Such causative agents can include, but are not limited to, bacterial, viral, fungal causative agents and the like.

The term "pathogen binding site" as used herein means a region or area where an enzyme can attach itself to a compound and react with it. In the present disclosure, the preferred pathogen binding site is one having at least one glycan structure substituted with at least one alpha-1,2-L-fucose moiety.

The term "F18$^+$ E. Coli" means any E. coli capable of expressing F18 fimbriae.

The genus "Bacillus", as used herein, includes all species within the genus "Bacillus," as known to those of skill in the art, including but not limited to B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. gibsonii, and B. thuringiensis. It is recognized that the genus Bacillus continues to undergo taxonomical reorganization. Thus, it is intended that the genus include species that have been reclassified, including but not limited to such organisms as Bacillus stearothermophilus, which is now named "Geobacillus stearothermophilus", or Bacillus polymyxa, which is now "Paenibacillus polymyxa" The production of resistant endospores under stressful environmental conditions is considered the defining feature of the genus Bacillus, although this characteristic also applies to the recently named Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus, and Virgibacillus.

A "feed" and a "food," respectively, means any natural or artificial diet, meal or the like or components of such meals intended or suitable for being eaten, taken in, digested, by a non-human animal and a human being, respectively.

As used herein, the term "food" is used in a broad sense—and covers food and food products for humans as well as food for non-human animals (i.e. a feed).

The term "feed" is used with reference to products that are fed to animals in the rearing of livestock. The terms "feed" and "animal feed" are used interchangeably. In a preferred embodiment, the food or feed is for consumption by non-ruminants and ruminants.

The term "direct fed microbial" ("DFM") as used herein is source of live (viable) naturally occurring microorganisms. Categories of DFMs include Bacillus, Lactic Acid Bacteria and Yeasts. Bacillus are unique, gram-positive rods that form spores. These spores are very stable and can withstand environmental conditions such as heat, moisture and a range of pH. These spores germinate into active vegetative cells when ingested by an animal and can be used in meal and pelleted diets. Lactic Acid Bacteria are gram-positive cocci that produce lactic acid which are antagonistic to pathogens. Since Lactic Acid Bacteria appear to be somewhat heat-sensitive, they are not used in pelleted diets. Types of Lactic Acid Bacteria include Bifidobacterium, Lactobacillus and Streptococcus. Yeasts are not bacteria. These microorganisms belong to the plant group fungi.

The term "protease" as used herein refers to an enzyme capable of cleaving a peptide bond. The terms "protease", "peptidase" and "proteinase" can be used interchangeably. Proteases can be found in animals, plants, bacteria, archaea and viruses. Proteolysis can be achieved by enzymes currently classified into six broad groups: aspartic proteases, cysteine proteases, serine proteases, threonine proteases, glutamic proteases, and metalloproteases.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. The terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

The terms "peptides", "proteins" and "polypeptides are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

Mutations can be named by the one letter code for the parent amino acid, followed by a position number and then the one letter code for the variant amino acid. For example, mutating glycine (G) at position 87 to serine (S) is represented as "G087S" or "G87S".

The term "mature" form of a protein, polypeptide, or peptide refers to the functional form of the protein, polypeptide, or enzyme without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

A "prosequence" or "propeptide sequence" refers to an amino acid sequence between the signal peptide sequence and mature enzyme sequence (e.g., a fucosidase) that is necessary for the proper folding and secretion of an enzyme; they are sometimes referred to as intramolecular chaperones. Cleavage of the prosequence or propeptide sequence results in a mature active enzyme which are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported. The gene of interest may be expressed with or without a signal sequence.

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question.

The term "amino acid" refers to the basic chemical structural unit of a protein or polypeptide. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

The term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

The term "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "coding sequence" refers to a nucleotide sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The terms "regulatory sequence" or "control sequence" are used interchangeably herein and refer to a segment of a nucleotide sequence which is capable of increasing or decreasing expression of specific genes within an organism. Examples of regulatory sequences include, but are not limited to, promoters, signal sequence, operators and the like. As noted above, regulatory sequences can be operably linked in sense or antisense orientation to the coding sequence/gene of interest.

"Promoter" or "promoter sequences" refer to DNA sequences that define where transcription of a gene by RNA polymerase begins. Promoter sequences are typically located directly upstream or at the 5' end of the transcription initiation site. Promoters may be derived in their entirety from a native or naturally occurring sequence, or be composed of different elements derived from different promoters found in nature, or even comprise synthetic DNA segments. It is understood by those skilled in the art that different promoters may direct the expression of a gene in different tissues or cell type or at different stages of development, or in response to different environmental or physiological conditions ("inducible promoters").

The "3' non-coding sequences" refer to DNA sequences located downstream of a coding sequence and include sequences encoding regulatory signals capable of affecting mRNA processing or gene expression, such as termination of transcription.

The term "transformation" as used herein refers to the transfer or introduction of a nucleic acid molecule into a host organism. The nucleic acid molecule may be introduced as a linear or circular form of DNA. The nucleic acid molecule may be a plasmid that replicates autonomously, or it may integrate into the genome of a production host. Production hosts containing the transformed nucleic acid are referred to as "transformed" or "recombinant" or "transgenic" organisms or "transformants".

The term "recombinant" as used herein refers to an artificial combination of two otherwise separated segments of nucleic acid sequences, e.g., by chemical synthesis or by the manipulation of isolated segments of nucleic acids by genetic engineering techniques. For example, DNA in which one or more segments or genes have been inserted, either naturally or by laboratory manipulation, from a different molecule, from another part of the same molecule, or an artificial sequence, resulting in the introduction of a new sequence in a gene and subsequently in an organism. The terms "recombinant", "transgenic", "transformed", "engineered" or "modified for exogenous gene expression" are used interchangeably herein.

The terms "recombinant construct", "expression construct", "recombinant expression construct" and "expression cassette" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The terms "production host", "host" and "host cell" are used interchangeably herein and refer to any organism, or cell thereof, whether human or non-human into which a recombinant construct can be stably or transiently introduced in order to express a gene. This term encompasses any progeny of a parent cell, which is not identical to the parent cell due to mutations that occur during propagation.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence. As used herein, "homologous proteins" or "homologous enzymes" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences.

Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein END-GAP=−1, protein GAPDIST=4, and KTUPLE=1. In one embodiment, a fast or slow alignment is used with the default settings where a slow alignment. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

Various polypeptide amino acid sequences and polynucleotide sequences are disclosed herein as features of certain aspects. Variants of these sequences that are at least about 70-85%, 85-90%, or 90%-95% identical to the sequences disclosed herein may be used in certain embodiments. Alternatively, a variant polypeptide sequence or polynucleotide sequence in certain embodiments can have at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequence, or at least about 85%, 86%, 87%, 88%, 89%, 90%, 91%, 92%, 93%, 94%, 95%, 96%, 97%, 98%, or 99% of the function of the disclosed sequence.

The term "variant", with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. The terms "expression cassette" and "expression vector are used interchangeably herein and refer to a specific vector containing a gene and having elements in addition to the gene that allow for expression of that gene in a host.

The term "expression", as used herein, refers to the production of a functional end-product (e.g., an mRNA or a protein) in either precursor or mature form. Expression may also refer to translation of mRNA into a polypeptide.

Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals. "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms The expression vector can be one of any number of vectors or cassettes useful for the transformation of suitable production hosts known in the art. Typically, the vector or cassette will include sequences directing transcription and translation of the relevant gene, a selectable marker, and sequences allowing autonomous replication or chromosomal integration. Suitable vectors generally include a region 5' of the gene which harbors transcriptional initiation controls and a region 3' of the DNA fragment which controls transcriptional termination. Both control regions can be derived from homologous genes to genes of a transformed production host cell and/or genes native to the production host, although such control regions need not be so derived.

As used herein, "homologous proteins" or "homologous enzymes" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=TUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

As used herein, the term "functional assay" refers to an assay that provides an indication of a protein's activity. In some embodiments, the term refers to assay systems in which a protein is analyzed for its ability to function in its usual capacity. For example, in the case of an alpha-L-fucosidase, a functional assay can involve determining the effectiveness of the alpha-L-fucosidase to hydrolyze an alpha-L-fucoside substrate.

L-Fucose-containing glycoconjugates are important for a myriad of physiological and pathological activities, such as inflammation, bacterial and viral infections, etc.

Fucosylated glycans are common within the gastrointestinal tract where they are found on cell surfaces and on mucins. Mucins are high molecular weight, heavy glycosylated proteins found in both a membrane-associated and a secreted form.

The presence or absence of intestinal receptors for F18 is genetically controlled. It has been demonstrated that susceptibility to colonisation by F18 bearing $E.$ $coli$ in oedema disease is controlled by a dominant allele and resistance by a recessive allele (Vogeli et al. (1996) Anim Genet. 27(5): 321-8).

The gene controlling expression of the $E.$ $coli$ F18 receptor has been shown to be linked to the alpha (1,2 L-fucosyltransferase 1 genes (FUT1). The FUT1 gene encodes galactoside 2-alpha-L-fucosyltransferase that modifies glycan terminals where adhesion occurs.

ETEC resistant animals have shown significantly lower levels of the FUT1 enzyme (Francis D H (2002) J Swine Health Prod. 10(4):171-5; Meijerink et al. (1997) Mammalian Genome 8:736-41). Fucosyltransferases have been shown to be involved in fucosylation of gut epithelium, and furthermore, the level of fucosylation varies during development of the animal (Torres-Pinedo and Mahmood (2004) Biochem Biophys Res Commun 125:546-53; Ruggiero-Lopez et al. (1991) Biochem J 279:801-6; Biol et al. (1987) Pediatr Res 22:250-6).

Blood group antigens are surface markers on red blood cell membranes. They are generally defined as molecules formed by sequential addition of saccharides to the carbohydrate side chains of lipids and proteins detected on erythrocytes and certain epithelial cells including those that line the gastrointestinal, urinary and respiratory tracts.

Specific oligosaccharide antigens attach to the proteins and lipids on the surface of erythrocytes. The most basic oligosaccharide attached is called the O antigen (also referred to as the H antigen). Human blood groups depend on the functioning of glycosyltransferases, enzymes that catalyze the formation of glycosidic bonds between monosaccharides. Specific oligosaccharide antigens attach to the proteins and lipids on the surface of erythrocytes.

This O (or H) antigen is the base oligosaccharide found in all three blood types AB, A, and B. The O antigen is of the form (-Lipid-Glucose-Galactose-N-acetylglucosamine-Galactose-Fucose). Blood type O only has the O antigen attached to the red blood cells.

It has been found that alpha-1-2Fucosyltransferases are necessary for formation of the blood group antigens. The O or H-antigen is a fucose, alpha-1,2-linked to a galactose. In blood group A-antigens, a GalNAc is added to the galactose in the H-antigen. H- and A-antigens are present in humans and pigs.

Figure 9:
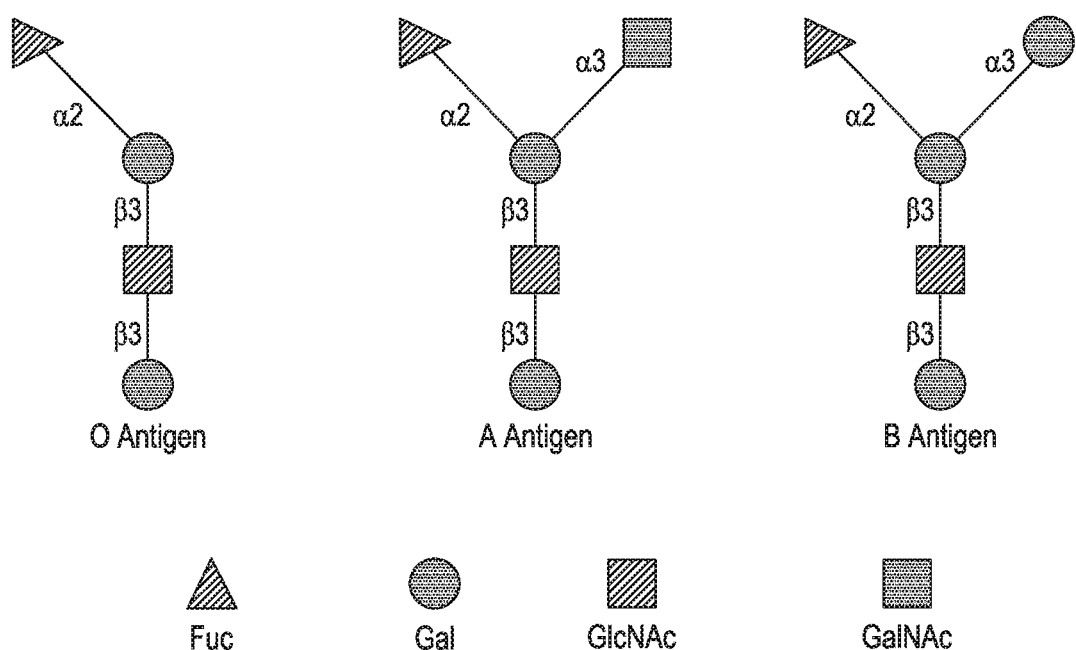
FIG. 9 depicts the terminal structure of the A B and O antigens.

The immunodominant monosaccharide that determines blood group A specificity is a terminal alpha-1,3-linked N-acetylgalactosamine (GalNAc), whereas the corresponding monosaccharide of blood group B specificity is an alpha-1,3-linked galactose (Gal). Group O cells lack both of these monosaccharides at the termini of their oligosaccharide chains, which instead are terminated with alpha-1,2-linkedfucose (Fuc) residues and designated the H antigen FIG. 9 depicts the terminal structure of the A B and O antigens. It should be noted that although best known as blood antigens these antigens are expressed on most tissues of the body and on epithelial and endothelial cells.

FIG. 10 depicts the structural basis of ABO blood group antigens. The A and B trisaccharide epitopes are formed from the common H disaccharide substrate alpha-1,3-N-acetylgalactosiaminyltransferase (GTA) and alpha-galactosyltransferase (GTB). Conversely, the strategy used for enzymatic conversion of blood group A and B antigens to H involves exoglycosidases that specifically hydrolyze the alpha-1,3-GalNAc (using an alpha-N-acetylgalactosidase, A-zyme) or the alpha-1,3-galactose (using an alpha-galactosidase, B-zyme) for form the common H structure found on O RBCs.

As is demonstrated in the Examples below, it appears that alpha-L-fucosidase is capable of removing a fucose residue from an H1 antigen trisaccharide but appears to have difficulties in removing a fucose residue from an A antigen tetrasaccharide which may possibly be due to steric hindrance. However, it is believed that when alpha-L-fucosidase is combined with an enzyme capable of removing an alpha-N-acetylgalactosylamine-containing moiety then the alpha-L-fucosidase can remove the fucose from an A antigen glucan-containing structure.

It may also be possible to convert blood group B antigens to H antigens using an alpha-galactosidase. Examples of such enzymes capable of removing an alpha-N-acetylgalactosylamine-containing moiety from a glucan-containing structure include but are not limited to N-acetylgalactosaminidase available from New England Biolabs, (#P0734).

The present disclosure relates to a method of preventing and/or treating an animal from having an intestinal pathogenic infection and/or diarrhea wherein the pathogenic infection and/or diarrhea is caused by a pathogen capable of binding to animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site.

Also within the scope of this disclosure are compositions for preventing and/or treating an animal from having an intestinal pathogenic infection and/or diarrhea wherein the pathogenic infection and/or diarrhea is caused by a pathogen capable of binding to animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site.

In all aspects disclosed herein (the method, composition or uses thereof), an alpha-L-fucosidase is capable of removing a terminal alpha-1,2-linked fucose group from a glycan-containing structure either alone or in combination with an enzyme capable of removing an N-acetyl-galactosylamine-containing moiety from a glycan-containing structure. This is discussed further in the Examples below.

Without being bound by theory, it is believed that hydrolysis of terminal alpha1,2 linkedfucose prevents adhesion to intestinal cells, e.g., as in the case of F18 fimbria expressed by ETEC.

Any enzyme, such as a glycoside hydrolase, capable of removing at least one fucosyl moiety can be used whether the fucsoyl moiety is removed from the pathogen binding site or a larger portion of the pathogen binding site is removed so long as the fucosyl moiety is removed as well. Preferably, alpha-L-fucosidase polypeptides can be used. Glycoside hydrolases, such as alpha-L-fucosidase polypeptides, of the present disclosure include isolated, recombinant, substantially pure, or non-naturally occurring polypeptides.

Preferably, alpha-L-fucosidase polypeptides are from the glycoside hydrolase family 95 (GH95) or the glycoside hydrolase family 29 (G29). Most preferably, such alpha-L-fucosidase polypeptides are in the GH95 family.

It may be desirable to engineer alpha-L-fucosidase so that it is stable at low pH and is also stable to pepsin. Furthermore, it also may be desirable to engineer alpha-L-fucosidase to have a broader substrate specificity, e.g., to be capable or accepting A (and even B) blood group antigens as substrate. In other words, expanding substrate specificity so that an engineered alpha-L-fucosidase is capable of removing fucose residue from an A tetrasaccharide without the need for adding an alpha-N-acetylgalactosaminidase.

In some embodiments, the polypeptides are useful in preventing and/or treating pathogenic infection and can be incorporated into prophylactic and/or therapeutic compositions.

Suitable alpha-L-fucosidases can be derived from a variety of sources, such as from *Arcanobacterium, Bacillus, Bacteroides, Corynebacterium, Streptococcus, Dictyostelium, Fusarium, Aspergillus, Bifidobacterium, Ignisphaera, Mahella, Cellulophaga, Rubinisphaera, Niastella, Haliscomenobacter, Rhodopirellula, Mycobacterium, Clostridium, Flavobacteriaceae, Ktedonobacter, Listeria, Paludibacter, Prunus, Propionibacterium, Ruminococcus, Thermotoga, Xanthomonas,* and *Lactobacillus*. Examples of species from which alpha-L-fucosidase can be derived include *Arcanobacterium haemolyticum, Bacillus cereus, Bacillus thuringiensis, Bacillus* sp. TS-2, *Bacillus bataviensis, Bacillus niacini, Bacillus* sp. J13, *Bacillus* sp. J37, *Bacillus lehensis, Bacillus halodurans, Bacillus alcalophilus, Bacillus megaterium, Bacillus cellulosilyticus, Bacillus hemicellulosilyticus, Bacillus okuhidensis, Bacillus butanolivorans, Bacillus pseudalcaliphilus, Bacillus bogoriensis, Bacillus akibai, Bacillus fulminans, Bacteroides fragilis, Bacteroides helcogenes, Streptococcus mitis* B6, *Streptococcus pneumoniae, Dictyostelium discoideum, Flavobacteriaceae bacterium* S85, *Fusarium graminearum, Aspergillus niger, Bifidobacterium bifidum, Bifidobacterium longum, Ignispheaera aggregans, Mahella australiensis, Cellulophaga lytica, Cellulophaga algicola, Rubinisphaera brasinliensis, Niastella koreensis, Haliscomenobacter hydrossis, Rhodopirellula baltica, Mycobacterium tuberculosis, Clostridium perfringens, Ktedonobacter racemifer, Listeria monocytogenes, Paludibacter propionicigenes, Prunus dulcis, Propionibacterium acnes, Ruminococcus gnavus, Ruminococcus torques, Thermotoga maritima, Lactobacillus paracasei, Lactobacillus casei* and *Xanthomonas manihotis*.

In still other embodiment, any alpha-L-fucosidases can be used to practice the methods and compositions disclosed herein. For examples, polypeptides having a fucosidase activity can be derived from *Arcanobacterium haemolyticum, Bacillus cereus, Bacillus thuringiensis, Bacillus* sp. TS-2, *Bacillus bataviensis, Bacillus niacini, Bacillus* sp. J13, *Bacillus* sp. J37, *Bacillus lehensis, Bacillus halodurans, Bacillus alcalophilus, Bacillus megaterium, Bacillus cellulosilyticus, Bacillus hemicellulosilyticus, Bacillus okuhidensis, Bacillus butanolivorans, Bacillus pseudalcaliphilus, Bacillus bogoriensis, Bacillus akibai, Bacillus fulminans, Bacteroides fragilis, Bacteroides helcogenes, Streptococcus mitis* B6, *Streptococcus pneumoniae, Dictyostelium discoideum, Flavobacteriaceae bacterium* S85, *Fusarium graminearum, Aspergillus niger, Bifidobacterium bifidum, Bifidobacterium longum, Ignispheaera aggregans, Mahella australiensis, Cellulophaga lytica, Cellulophaga algicola, Rubinisphaera brasinliensis, Niastella koreensis, Haliscomenobacter hydrossis, Rhodopirellula baltica, Mycobacterium tuberculosis, Clostridium perfringens, Ktedonobacter racemifer, Listeria monocytogenes, Paludibacter propionicigenes, Prunus dulcis, Propionibacterium acnes, Ruminococcus gnavus, Ruminococcus torques, Thermotoga maritima, Lactobacillus paracasei, Lactobacillus casei* and *Xanthomonas manihotis*, or a sequence having at least 10%, 20%, 30%, 40%, 50%, 60%, 70%, 75%, 80%, 90%, 95%, 98%, 99% identity to the fucosidase sequence from *Arcanobacterium haemolyticum, Bacillus cereus, Bacillus thuringiensis, Bacillus* sp. TS-2, *Bacillus bataviensis, Bacillus niacini, Bacillus* sp. J13, *Bacillus* sp. J37, *Bacillus lehensis, Bacillus halodurans, Bacillus alcalophilus, Bacillus megaterium, Bacillus cellulosilyticus, Bacillus hemicellulosilyticus, Bacillus okuhidensis, Bacillus butanolivorans, Bacillus pseudalcaliphilus, Bacillus bogoriensis, Bacillus akibai, Bacillus fulminans, Bacteroides Bacteroides helcogenes, Streptococcus mitis* B6, *Streptococcus pneumoniae, Dictyostelium discoideum, Flavobacteriaceae bacterium* S85, *Fusarium graminearum, Aspergillus niger, Bifidobacterium bifidum, Bifidobacterium longum, Ignispheaera aggregans, Mahella australiensis, Cellulophaga lytica, Cellulophaga algicola, Rubinisphaera brasinliensis, Niastella koreensis, Haliscomenobacter hydrossis, Rhodopirellula baltica, Mycobacterium tuberculosis, Clostridium perfringens, Ktedonobacter racemifer, Listeria monocytogenes, Paludibacter propionicigenes, Prunus dulcis, Propionibacterium acnes, Ruminococcus gnavus, Ruminococcus torques, Thermotoga maritima, Lactobacillus paracasei, Lactobacillus casei* and *Xanthomonas manihotis*, or a polypeptide which differs from any of the above mentioned sequences by one or several amino acid additions, deletions and/or substitutions; or a polynucleotide which expresses any of the above fucosidase sequences.

Homology can be determined by amino acid sequence alignment, e.g., using a program such as BLAST, ALIGN, or CLUSTAL, as described herein. In some embodiments, the polypeptide is an isolated, recombinant, substantially pure, or non-naturally occurring enzyme that is capable of removing, at a minimum, at least one fucosyl moiety from the pathogen binding site. It is possible that this polypeptide could remove a larger portion of the pathogen binding site provided that the at least one fucosyl moiety is also removed. Preferably, the enzyme has alpha-L-fucosidase activity, or catalyzes the cleavage of a terminal alpha-1,2-linked fucose group from a polysaccharide such as an alpha-L-fucoside.

It will be apparent to the skilled person that full length and/or mature alpha-L-fucosidase can be made using any well-known technique in the art.

In another aspect any isolated, recombinant, substantially pure, synthetically derived, or non-naturally occurring nucleic acid comprising a nucleotide sequence encoding any polypeptide (including any fusion protein, etc.) that is capable of removing, at a minimum, at least one fucosyl moiety from the pathogen binding site. It is possible that this polypeptide could remove a larger portion of the pathogen binding site provided that the at least one fucosyl moiety is also removed.

Also of interest is a vector comprising a polynucleotide encoding a glucose hydrolase such as an alpha-L-fucosidase enzyme which hydrolyzes an L-fucose moiety from an alpha-1,2-L-fucoside.

It will be apparent to the skilled person that the vector can be any suitable expression vector and that the choice of vector may vary depending upon the type of cell into which the vector is to be inserted. Suitable vectors include pGAPT-PG, pRAX1, pGAMD, pGPT-pyrG1, pC194, pJH101, pE194, and pHP13 (See, Harwood and Cutting [eds.], Chapter 3, Molecular Biological Methods for *Bacillus*, John Wiley & Sons [1990]). See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624), and p2JM103BBI.

The expression vector can be one of any number of vectors or cassettes useful for the transformation of suitable production hosts known in the art. Typically, the vector or cassette will include sequences directing transcription and translation of the relevant gene, a selectable marker, and sequences allowing autonomous replication or chromosomal integration. Suitable vectors generally include a region 5' of the gene which harbors transcriptional initiation controls and a region 3' of the DNA fragment which controls transcriptional termination. Both control regions can be derived from homologous genes to genes of a transformed production host cell and/or genes native to the production host, although such control regions need not be so derived.

DNA fragments which control transcriptional termination may also be derived from various genes native to a preferred production host cell. In certain embodiments, the inclusion of a termination control region is optional. In certain embodiments, the expression vector includes a termination control region derived from the preferred host cell.

The expression vector can be included in the production host, particularly in the cells of microbial production hosts. The production host cells can be microbial hosts found within the fungal or bacterial families and which grow over a wide range of temperature, pH values, and solvent tolerances. For example, it is contemplated that any of bacteria, algae, and fungi such as filamentous fungi and yeast may suitably host the expression vector.

Inclusion of the expression vector in the production host cell may be used to express the protein of interest so that it may reside intracellularly, extracellularly, or a combination of both inside and outside the cell. Extracellular expression renders recovery of the desired protein from a fermentation product more facile than methods for recovery of protein produced by intracellular expression.

The recombinant expression vector may be any vector such as a plasmid or virus which can conveniently be subjected to recombinant DNA procedures and lead to expression of the nucleotide sequence. The vector choice will typically depend on the compatibility of the vector with the production host into which the vector is to be introduced. The vectors may be linear or closed circular plasmids. The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the production host, is integrated into the genome and replicated together with the chromosome(s) into which it has been integrated. Some non-limiting examples of such vectors is provided in the Fungal Genetics Stock Center Catalogue of Strains (FGSC, <www.fgsc.net»), Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press. 396-428 and U.S. Pat. No. 5,874, 276. Particularly useful vectors include pTREX, pFB6, pBR322, PUCI8, pUCI00 and pENTR/D. Suitable plasmids for use in bacterial cells include pBR322 and pUC19 permitting replication in *E. coli* and pE194 for example permitting replication in *Bacillus*.

Briefly with respect to production in production host cells reference can be made to Sambrook et al., (1989) supra, Ausubel (1987) supra, van den Hondel et al. (1991) in Bennett and Lasure (Eds.) MORE GENE MANIPULATIONS IN FUNGI, Academic Press (1991) pp. 70-76 and 396-428; Nunberg et al., (1984) *Mol. Cell Biol.* 4:2306-2315; Boel et al., (1984) 30 *EMBO J.* 3:1581-1585; Finkelstein in BIOTECHNOLOGY OF FILAMENTOUS FUNGI, Finkelstein et al. Eds. Butterworth-Heinemann, Boston, Mass. (1992), Chap. 6; Kinghorn et al. (1992) APPLIED MOLECULAR GENETICS OF FILAMENTOUS FUNGI, Blackie Academic and Professional, Chapman and Hall, London; Kelley et al., (1985) *EMBO J.* 4:475-479; Penttila et al., (1987) *Gene* 61: 155-164; and U.S. Pat. No. 5,874, 276. A list of suitable vectors may be found in the Fungal Genetics Stock Center Catalogue of Strains (FGSC, www at fgsc.net). Suitable vectors include those obtained from for example Invitrogen Life Technologies and Promega. Specific vectors suitable for use in fungal host cells include vectors such as pFB6, pBR322, pUC 18, pUC100, pDON™201, pDONR™221, pENTR™, pGEM®3Z and pGEM®4Z.

The vector system may be a single vector or plasmid or two or more vectors or plasmids which together contain the total DNA to be introduced into the genome of the host cell, or a transposon.

The vector may also contain one or more selectable markers to permit easy selection of the transformed cells. A selectable marker is a gene, the product of which provides for biocide or viral resistance and the like. Examples of selectable markers include ones which confer antimicrobial resistance. Nutritional markers also find use in the present invention including those markers known in the art as amdS, argB and pyr4. Markers useful for the transformation of *Trichoderma* are known in the art (see, e.g., Finkelstein, chapter 6, in Biotechnology of Filamentous Fungi, Finkelstein et al., EDS Butterworth-Heinemann, Boston Mass. (1992) and Kinghorn et al., (1992) Applied Molecular Genetics of Filamentous Fungi, Blackie Academic and Professional, Chapman and Hall, London). In some embodiments, the expression vectors will also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical; any of the many resistance genes known in the art are suitable. The prokaryotic sequences are preferably chosen such that they do not interfere with the replication or integration of the DNA in *Trichoderma reesei*.

The vector may also contain an element(s) permitting stable integration of the vector into the product host genome or autonomous replication of the vector in the production host independent of the genome of the cell. For integration into the host cell genome, the vector may rely on the nucleotide sequence encoding the aspartic protease or any other element of the vector for stable integration of the vector into the genome by homologous or nonhomologous recombination.

For autonomous replication, the vector may further comprise an origin of replication enabling the vector to replicate autonomously in the production host.

More than one copy of the nucleotide sequence encoding an alpha-L-fucosidase may be inserted into the production host to increase production of the alpha-L-fucosidase. An increase in the copy number of the nucleotide sequence can be obtained by integrating at least one additional copy of the sequence into the genome of the production host or by including an amplifiable selectable marker gene, and thereby additional copies of the nucleotide sequence can be selected for by culturing the production host cells in the presence of an appropriate selectable agent.

A vector comprising the nucleotide sequence encoding an alpha-L-fucosidase is introduced into the production host so that the vector is maintained as a chromosomal integrant or as a self-replicating extra-chromosomal vector. Integration is generally considered to be an advantage as the nucleotide sequence is more likely to be stably maintained the production host. Integration of the vector into the production host chromosome may occur by homologous or nonhomologous recombination as was discussed above.

Exemplary vectors include, but are not limited to pGXT (the same as the pTTTpyr2 vector as described in published PCT application WO2015/017256). There can also be mentioned standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Examples of suitable expression and/or integration vectors are provided in Sambrook et al., (1989) supra, Bennett and Lasure (Eds.) More Gene Manipulations in Fungi, (1991) Academic Press pp. 70-76 and pp. 396-428 and articles cited therein; U.S. Pat. No. 5,874,276 and Fungal Genetic Stock Center Catalogue of Strains, (FGSC, www.fgsc.net.). Useful vectors may be obtained from Promega and Invitrogen. Some specific useful vectors include pBR322, pUC18, pUC100, pDON™201, pENTR™, pGEN®3Z and pGEN®4Z. However, other forms of expression vectors which serve equivalent functions and which are, or become, known in the art can also be used. Thus, a wide variety of host/expression vector combinations may be employed in expressing the DNA sequences disclosed herein. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage .lambda., e.g., NM989, and other DNA phages, e.g., M13 and filamentous single stranded DNA phages, yeast plasmids such as the 2.mu plasmid or derivatives thereof.

The choice of a production host can be any suitable microorganism such as bacteria, fungi and algae. Typically, the choice will depend upon the gene encoding the glycoside hydrolase of interest such as an alpha-L-fucosidase.

Examples of suitable production hosts include, but are not limited to, bacterial, fungal, plant cells etc. Preferably, the production host may be selected from E. coli, Streptomyces, Hansenula, Trichoderma (particularly T. reesei), Bacillus, Lactobacillus, Aspergillus (particularly A. niger), a plant cell and/or spores of Bacillus, Trichoderma, or Aspergillus.

In some embodiments, a recombinant alpha-L-fucosidase enzyme may be used in the methods and compositions disclosed herein. In a preferred aspect, there is provided a food or feed additive comprising an alpha-L-fucosidase enzyme which is capable of hydrolyzing L-fucose from an alpha-L-fucosidase.

Many standard transfection methods can be used to produce bacterial and filamentous fungal (e.g. Aspergillus or Trichoderma) cell lines that express large quantities of the desired glycoside hydrolase such as an alpha-L-fucosidase. Some of the published methods for the introduction of DNA constructs into cellulase-producing strains of Trichoderma include Lorito, Hayes, DiPietro and Harman, (1993) Curr. Genet. 24: 349-356; Goldman, VanMontagu and Herrera-Estrella, (1990) Curr. Genet. 17:169-174; and Penttila, Nevalainen, Ratto, Salminen and Knowles, (1987) Gene 6: 155-164, also see U.S. Pat. Nos. 6,022,725; 6,268,328 and Nevalainen et al., "The Molecular Biology of Trichoderma and its Application to the Expression of Both Homologous and Heterologous Genes" in Molecular Industrial Mycology, Eds, Leong and Berka, Marcel Dekker Inc., NY (1992) pp 129-148; for Aspergillus include Yelton, Hamer and Timberlake, (1984) Proc. Natl. Acad. Sci. USA 81: 1470-1474, for Fusarium include Bajar, Podila and Kolattukudy, (1991) Proc. Natl. Acad. Sci. USA 88: 8202-8212, for Streptomyces include Hopwood et al., 1985, Genetic Manipulation of Streptomyces: Laboratory Manual, The John Innes Foundation, Norwich, UK and Fernandez-Abalos et al., Microbiol 149:1623-1632 (2003) and for Bacillus include Brigidi, DeRossi, Bertarini, Riccardi and Matteuzzi, (1990) FEMS Microbiol. Lett. 55: 135-138).

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). Also of use is the Agrobacterium-mediated transfection method described in U.S. Pat. No. 6,255,115. It is only necessary that the particular genetic engineering procedure used be capable of successfully introducing at least one gene into the host cell capable of expressing the gene.

Depending upon the host cell used post-transcriptional and/or post-translational modifications may be made. One non-limiting example of a post-transcriptional and/or post-translational modification is "clipping" or "truncation" of a polypeptide. For example, this may result in taking a glycoside hydrolase as described herein such as an alpha-L-fucosidase from an inactive or substantially inactive state to an active state as in the case of a pro-peptide undergoing further post-translational processing to a mature peptide having the enzymatic activity. In another instance, this clipping may result in taking a mature a glycoside hydrolase as described herein such as an alpha-L-fucosidase polypeptide and further removing N or C-terminal amino acids to generate truncated forms of the alpha-L-fucosidase that retain enzymatic activity.

Other examples of post-transcriptional or post-translational modifications include, but are not limited to, myristoylation, glycosylation, truncation, lipidation and tyrosine, serine or threonine phosphorylation. The skilled person will appreciate that the type of post-transcriptional or post-translational modifications that a protein may undergo may depend on the host organism in which the protein is expressed.

Transformation methods for Aspergillus and Trichoderma are described in, for example, Yelton et al. (1984) Proc. Natl. Acad. Sci. USA 81: 1470-1474; Berka et al., (1991) in Applications of Enzyme Biotechnology, Eds. Kelly and Baldwin, Plenum Press (NY); Cao et al., (2000) Sci. 9:991-1001; Campbell et al., (1989) Curro Genet. 16:53-56; Pentilla et al., (1987) Gene 61:155-164); de Groot et al., (1998) Nat. Biotechnol. 16:839-842; U.S. Pat. Nos. 6,022,725; 6,268,328 and EP 238 023. The expression of heterologous protein in Trichoderma is described in U.S. Pat. Nos. 6,022,725; 6,268,328; Harkki et ale (1991); Enzyme Microb. Technol. 13:227-233; Harkki et al., (1989) Bio Technol. 7:596-603; EP 244,234; EP 215,594; and Nevalainen et al., "The Molecular Biology of Trichoderma and its Application to the Expression of Both Homologous and Heterologous Genes", in MOLECULAR INDUSTRIAL MYCOLOGY, Eds. Leong and Berka, Marcel Dekker Inc., NY (1992) pp. 129-148). Reference is also made to W096100787 and Bajar et al., (1991) Proc. Natl. Acad. Sci. USA 88:8202-28212 for transformation of Fusarium strains.

After the expression vector is introduced into the cells, the transfected or transformed cells are cultured under conditions favoring expression of genes under control of the promoter sequences. In some instances, the promoter sequence is the cbh1 promoter. Large batches of transformed cells can be cultured as described in Ilmen et al 1997 ("Regulation of cellulase gene expression in the filamentous fungus Trichoderma reesei." Appl. Envir. Microbiol. 63:1298-1306).

Uptake of DNA into the host Trichoderma sp. strain depends upon the calcium ion concentration. Generally, about 10-50 mM $CaCl_2$) is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethyleneglycol is believed to fuse the cell membranes, thus permitting the contents of the medium to be delivered into the cytoplasm of the Trichoderma sp. strain. This fusion frequently leaves multiple copies of the plasmid DNA integrated into the host chromosome.

Usually transformation of Trichoderma sp. uses protoplasts or cells that have been subjected to a permeability treatment, typically at a density of $10^5$ to $10^7$/mL, particularly $2 \times 10^6$/mL. A volume of 100 µL of these protoplasts or cells in an appropriate solution (e.g., 1.2 M sorbitol and 50 mM $CaCl_2$)) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

The medium used to cultivate the cells may be any conventional medium suitable for growing the host cell and obtaining expression of an alpha-fucosidase polypeptide. Suitable media and media components are available from commercial suppliers or may be prepared according to published recipes (e.g., as described in catalogues of the American Type Culture Collection).

In some embodiments, the preparation of a spent whole fermentation broth of a recombinant microorganism can be achieved using any cultivation method known in the art resulting in the expression of enzyme of interest. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the enzyme to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

Host cells may be cultured under suitable conditions that allow expression of an alpha-glucosidase. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or sophorose.

Polypeptides can also be produced recombinantly in an in vitro cell-free system, such as the TNT™ (Promega) rabbit reticulocyte system. An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired alpha-glucosidase. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of the enzyme of interest, such as, a fucosidase. Since production hosts and transformed cells can be cultured in conventional nutrient media. The culture media for transformed host cells may be modified as appropriate for activating promoters and selecting transformed cells. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; www.atcc.org).

Any of the fermentation methods well known in the art can suitably be used to ferment the transformed or the derivative fungal strain as described above.

A classical batch fermentation is a closed system, where the composition of the medium is set at the beginning of the fermentation, and the composition is not altered during the fermentation. At the beginning of the fermentation, the medium is inoculated with the desired organism(s). In other words, the entire fermentation process takes place without addition of any components to the fermentation system throughout.

Alternatively, a batch fermentation qualifies as a "batch" with respect to the addition of the carbon source. Moreover, attempts are often made to control factors such as pH and oxygen concentration throughout the fermentation process. Typically the metabolite and biomass compositions of the batch system change constantly up to the time the fermentation is stopped. Within batch cultures, cells progress through a static lag phase to a high growth log phase and finally to a stationary phase, where growth rate is diminished or halted. Left untreated, cells in the stationary phase would eventually die. In general, cells in log phase are responsible for the bulk of production of product. A suitable variation on the standard batch system is the "fed-batch fermentation" system. In this variation of a typical batch system, the substrate is added in increments as the fermentation progresses. Fed-batch systems are useful when it is known that catabolite repression would inhibit the metabolism of the cells, and/or where it is desirable to have limited amounts of substrates in the fermentation medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are well known in the art.

Continuous fermentation is another known method of fermentation. It is an open system where a defined fermentation medium is added continuously to a bioreactor, and an equal amount of conditioned medium is removed simultaneously for processing. Continuous fermentation generally maintains the cultures at a constant density, where cells are maintained primarily in log phase growth. Continuous fermentation allows for the modulation of one or more factors that affect cell growth and/or product concentration. For example, a limiting nutrient, such as the carbon source or nitrogen source, can be maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Separation and concentration techniques are known in the art and conventional methods can be used to prepare a concentrated solution or broth comprising an alpha-glucosidase polypeptide of the invention.

After fermentation, a fermentation broth is obtained, the microbial cells and various suspended solids, including residual raw fermentation materials, are removed by conventional separation techniques in order to obtain an enzyme-containing solution. Filtration, centrifugation, microfiltration, rotary vacuum drum filtration, ultrafiltration, centrifugation followed by ultra-filtration, extraction, or chromatography, or the like, are generally used.

It may at times be desirable to concentrate a solution or broth comprising an polypeptide of interest to optimize recovery. Use of un-concentrated solutions or broth would typically increase incubation time in order to collect the enriched or purified enzyme precipitate.

The enzyme-containing solution can be concentrated using conventional concentration techniques until the desired enzyme level is obtained. Concentration of the enzyme containing solution may be achieved by any of the techniques discussed herein. Examples of methods of enrichment and purification include but are not limited to rotary vacuum filtration and/or ultrafiltration.

A glycoside hydrolase as described herein such as an alpha-L-fucosidase enzyme as described herein can be tested for activity using a variety of tests known in the art. For example, activity can be tested by combining the enzyme with glycoprotein or oligosaccharide and water as necessary. Activity can be measured by analysis of reaction products, which can be separated and visualized, for example, by thin layer chromatography or spectrophotometry. An example of a fucose spectrophotometric assay is the Megazyme K-FU-COSE kit (Cao et al. (2014) J Biol Chem 289(37):25624-38.

The method disclosed herein further comprises administering to the animal an effective amount of a glycoside hydrolase such as an alpha-L-fucosidase in combination with at least one direct fed microbial alone or in combination with least one protease.

Furthermore, a glycoside hydrolase as described herein such as an alpha-L-fucosidase, either alone or in combination with at least one direct fed microbial alone and/or in combination with least one protease may be encapsulated for use in animal feed or a premix. In addition, a glycoside hydrolase as described herein such as an the alpha-L-fucosidase, either alone or in combination with at least one direct fed microbial alone and/or in combination with least one protease, whether or not encapsulated, may be in the form of a granule.

It is believed that a glycoside hydrolase as described herein such as an alpha-L-fucosidase enzyme as described herein may be used in combination with one or more additional enzymes. In some embodiments, the one or more additional enzymes is selected from the group consisting of those involved in protein degradation including carboxypeptidases preferably carboxypeptidase A, carboxypeptidase Y, A. niger aspartic acid proteases of PEPAa, PEPAb, PEPAc and PEPAd, elastase, amino peptidases, pepsin or pepsin-like, trypsin or trypsin-like proteases, acid fungal proteases and bacterial proteases including subtilisin and its variants, and of those involved in starch metabolism, fibre degradation, lipid metabolism, proteins or enzymes involved in glycogen metabolism, enzymes which degrade other contaminants, acetyl esterases, amylases, arabinases, arabinofuranosidases, exo- and endo-peptidases, catalases, cellulases, chitinases, chymosin, cutinase, deoxyribonucleases, epimerases, esterases, formamidase, -galactosidases, for example α or β-galactosidases, exo-glucanases, glucan lyases, endo-glucanases, glucoamylases, glucose oxidases, glucosidases, for example α or β-glucosidases, glucuronidases, hemicellulases, hydrolases, invertases, isomerases, laccases, phenol oxidases, lipase, lyases, mannosidases, oxidases, oxidoreductases, pectinase, pectate lyases, pectin acetyl esterases, pectin depolymerases, peptidase, pectin methyl esterases, pectinolytic enzymes, peroxidases, phenoloxidases, phytase, polygalacturonases, rhamno-galacturonases, ribonucleases, thaumatin, transferases, transport proteins, transglutaminases, xylanases, hexose oxidase (D-hexose: (3/4-oxidoreductase, EC 1.1.3.5), acid phosphatases and/or others or combinations thereof. These include enzymes that, for example, modulate the viscosity of the composition or feed.

Furthermore, a glycoside hydrolase as described herein such as an alpha-L-fucosidase may be encapsulated so as to withstand the acid pH found in the stomach.

The glycoside hydrolase as described herein such as an alpha-L-fucosidase, whether or not encapsulated, may be used alone or in combination with at least one direct fed microbial and may be administered in an animal feed or premix.

The glycoside hydrolase as described herein such as an alpha-L-fucosidase, whether or not encapsulated, may be used alone or in combination with at least one direct fed microbial and at least one protease and may be administered in an animal feed or premix.

Furthermore, the glycoside hydrolase as described herein such as an alpha-L-fucosidase, whether or not encapsulated, may be used alone or in combination with at least one direct fed microbial and may be administered in an animal feed or premix and the alpha-L-fucosidase may be in the form of a granule or liquid. The preferred form is a granule.

Also included within the scope of this disclosure are compositions for preventing and/or treating an animal having an intestinal pathogenic infection and/or diarrhea wherein the pathogenic infection is caused by a pathogen capable of binding to an animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site.

As was noted above, a glycoside hydrolase such as an alpha-L-fucosidase should be capable of removing a terminal alpha-1,2-linked fucose group from a glycan-containing structure either alone or in combination with an enzyme capable of removing an N-acetyl-galactosylamine-containing moiety from a glycan-containing structure. Preferably, the alpha-L-fucosidase is selected from the group consisting of glycoside hydrolase family 95 (GH95) and glycoside hydrolase family 29 (GH 29) and, most preferably, the alpha-L-fucosidase is selected from the group consisting of glycoside hydrolase family 95 (GH95).

This composition may be used to prevent and/or treat any intestinal pathogenic infection as was discussed above. One pathogen of interest is *Escherichia coli* expressing F18 fimbriae.

It is clear from the foregoing discussion that the composition may further comprise at least one direct fed microbial either alone or in combination with at least one protease.

A glycoside hydrolase, such as an alpha-L-fucosidase, either alone or in combination with at least one direct fed microbial alone and/or in combination with least one protease may be encapsulated for use in animal feed or a premix. In addition, a glycoside hydrolase, such as an alpha-L-fucosidase, either alone or in combination with at least one direct fed microbial alone and/or in combination with least one protease, whether or not encapsulated, may be in the form of a granule.

Animal feeds may include plant material such as corn, wheat, sorghum, soybean, canola, sunflower or mixtures of any of these plant materials or plant protein sources for poultry, pigs, ruminants, aquaculture and pets. It is contemplated that animal performance parameters, such as growth, feed intake and feed efficiency, but also improved uniformity, reduced ammonia concentration in the animal house and consequently improved welfare and health status of the animals will be improved. More specifically, as used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

The terms "animal feed," "feed", "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

When used as, or in the preparation of, a feed, such as functional feed, the enzyme or feed additive composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

In a preferred embodiment the enzyme or feed additive composition of the present invention is admixed with a feed component to form a feedstuff. The term "feed component" as used herein means all or part of the feedstuff. Part of the feedstuff may mean one constituent of the feedstuff or more than one constituent of the feedstuff, e.g. 2 or 3 or 4 or more. In one embodiment the term "feed component" encompasses a premix or premix constituents. Preferably, the feed may be a fodder, or a premix thereof, a compound feed, or a premix thereof. A feed additive composition according to the present invention may be admixed with a compound feed, a compound feed component or to a premix of a compound feed or to a fodder, a fodder component, or a premix of a fodder.

Any feedstuff described herein may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grains (DDG) (particularly corn based Distillers Dried Grains (cDDG)), Distillers Dried Grains with Solubles (DDGS) (particularly corn based Distillers Dried Grains with Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

The term "fodder" as used herein means any food which is provided to an animal (rather than the animal having to forage for it themselves). Fodder encompasses plants that have been cut. Furthermore, fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

In one embodiment the feedstuff comprises or consists of corn, DDGS (such as cDDGS), wheat, wheat bran or any combination thereof.

In one embodiment the feed component may be corn, DDGS (e.g. cDDGS), wheat, wheat bran or a combination thereof. In one embodiment the feedstuff comprises or consists of corn, DDGS (such as cDDGS) or a combination thereof.

A feedstuff described herein may contain at least 30%, at least 40%, at least 50% or at least 60% by weight corn and soybean meal or corn and full fat soy, or wheat meal or sunflower meal.

For example, a feedstuff may contain between about 5 to about 40% corn DDGS. For poultry, the feedstuff on average may contain between about 7 to 15% corn DDGS. For swine (pigs), the feedstuff may contain on average 5 to 40% corn DDGS. It may also contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff also may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wet-cake, Distillers Dried Grains (DDG), Distillers Dried Grains with Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton. In one aspect, the feedstuff as described herein comprises at least one high fibre material and/or at least one by-product of the at least one high fibre feed material selected from the group consisting of Distillers Dried Grains with Solubles (DDGS), particularly cDDGS, wet-cake, Distillers Dried Grains (DDG), particularly cDDG, wheat bran, and wheat for example. In one embodiment the feedstuff of the present invention comprises at least one high fibre material and/or at least one by-product of the at least one high fibre feed material selected from the group consisting of Distillers Dried Grains with Solubles (DDGS), particularly cDDGS, wheat bran, and wheat for example.

The feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" as used herein encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

Animal feed can also include a fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

In still another aspect, animal feed encompasses bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of a glycoside hydrolase as described herein such as an alpha-L-fucosidase (or composition comprising a glycoside hydrolase as described herein such as an alpha-L-fucosidase) to a product (e.g. the feed). Examples of application methods which may be used, include, but are not limited to, treating the product in a material comprising the feed additive composition, direct application by mixing the feed additive composition with the product, spraying the feed additive composition onto the product surface or dipping the product into a preparation of the feed additive composition. In one embodiment the feed additive composition of the present invention is preferably admixed with the product (e.g. feedstuff). Alternatively, the feed additive composition may be included in the emulsion or raw ingredients of a feedstuff. This allows the composition to impart a performance benefit.

The term "thermally stable" means that at least about 50%, 55%, 60%, 65%, 70%, 75%, 80%, 85%, 90%, 95%, 96%, 97% or 98% of the enzyme that was present/active in the additive before heating to the specified temperature is still present/active after it cools to room temperature. Preferably, at least about 80% of the enzyme that is present and active in the additive before heating to the specified temperature is still present and active after it cools to room temperature.

It is also possible that alpha-L-fucosidases (or a composition comprising alpha-L-fucosidases) described herein can be homogenized to produce a powder.

In an alternative preferred embodiment, a glycoside hydrolase as described herein such as an alpha-L-fucosidase (or composition comprising a glycoside hydrolase as described herein such as an alpha-L-fucosidase) can be formulated to granules as described in WO2007/044968 (referred to as TPT granules) or WO1997/016076 or WO1992/012645 incorporated herein by reference. "TPT" means Thermo Protection Technology.

In another aspect, when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme. Preferably, the salt used for the salt coating has a water activity greater than 0.25 or constant humidity greater than 60% at 20° C. In some embodiments, the salt coating comprises $Na_2SO_4$.

A method of preparing a glycoside hydrolase as described herein such as an alpha-L-fucosidase (or composition comprising a glycoside hydrolase as described herein such as an alpha-L-fucosidase) may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes., 5 minutes, 10 minutes, 15 minutes, 30 minutes and 1 hour. It will be understood that a glycoside hydrolase as described herein such as an alpha-L-fucosidase (or composition comprising a glycoside hydrolase as described herein such as an alpha-L-fucosidase) described herein are suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins. In some embodiments, the feedstuff is a corn soybean meal mix.

Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for pigs.

The feed additive composition and/or the feedstuff comprising the same may be used in any suitable form. The feed additive composition may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions may be mixed with feed or administered in the drinking water.

A feed additive composition, comprising admixing a fucosidase as taught herein with a feed acceptable carrier, diluent or excipient, and (optionally) packaging.

The feedstuff and/or feed additive composition may be combined with at least one mineral and/or at least one vitamin. The compositions thus derived may be referred to herein as a premix. The feedstuff may comprise at least 0.0001% by weight of the feed additive. Suitably, the feedstuff may comprise at least 0.0005%; at least 0.0010%; at least 0.0020%; at least 0.0025%; at least 0.0050%; at least 0.0100%; at least 0.020%; at least 0.100% at least 0.200%; at least 0.250%; at least 0.500% by weight of the feed additive.

Preferably, a food or feed additive composition may further comprise at least one physiologically acceptable carrier. The physiologically acceptable carrier is preferably selected from at least one of maltodextrin, limestone (calcium carbonate), cyclodextrin, wheat or a wheat component, sucrose, starch, Na[2]S0[4], Talc, PVA and mixtures thereof. In a further embodiment, the food or feed additive may further comprise a metal ion chelator. The metal ion chelator may be selected from EDTA or citric acid.

In some embodiments the food or feed additive composition comprises a glycoside hydrolase as described herein such as an alpha-L-fucosidase at a level of at least 0.0001 g/kg, 0.001 g/kg, at least 0.01 g/kg, at least 0.1 g/kg, at least 1 g/kg, at least 5 g/kg, at least 7.5 g/kg, at least 10.0 g/kg, at least 15.0 g/kg, at least 20.0 g/kg, at least 25.0 g/kg. In some embodiments, the food or feed additive comprises the alpha-L-fucosidase at a level such that when added to a food or feed material, the feed material comprises the alpha-L-fucosidase in a range of 1-500 mg/kg, 1-100 mg/kg, 2-50 mg/kg or 2-10 mg/kg. In some embodiments of the present invention the food or feed material comprises at least 100, 1000, 2000, 3000, 4000, 5000, 10000, 20000, 30000, 50000, 100000, 500000, 1000000 or 2000000 Units of glycoside hydrolase, such as an alpha-L-fucosidase per kilogram feed or food material. In some embodiments, one unit of $\alpha$-1,2-fucosidase activity can be defined as the amount of enzyme that can catalyze release of one $\mu$mole L-fucose per minute from 2'-fucosyllactose under the assay conditions described in Example 2.

Ranges can include, but are not limited to, any combination of the lower and upper ranges discussed above.

Formulations comprising any glycoside hydrolase as described herein such as alpha-L-fucosidases and compositions described herein may be made in any suitable way to ensure that the formulation comprises active enzymes. Such formulations may be as a liquid, a dry powder or a granule.

Preferably, the feed additive composition is in a solid form suitable for adding on or to a feed pellet.

Dry powder or granules may be prepared by means known to those skilled in the art, such as, high shear granulation, drum granulation, extrusion, spheronization, fluidized bed agglomeration, fluidized bed spray drying.

A glycoside hydrolase as described herein such as an alpha-L-fucosidases and compositions described herein may be coated, for example encapsulated. In one embodiment, the coating protects the enzymes from heat and may be considered a thermoprotectant. In one embodiment the coating protects the enzyme from low pH. EUDRAGIT® (methacrylate cationic synthetic polymers) is one example of a coating material that can be used.

Feed additive composition described herein can be formulated to a dry powder or granules as described in WO2007/044968 (referred to as TPT granules) or WO1997/016076 or WO1992/012645 (each of which is incorporated herein by reference).

In one embodiment animal feed may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

The feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

A granule may be produced using a steam-heated pelleting process which may be conducted between 85° C. and 95° C. for up to several minutes.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the enzyme(s) onto a carrier substrate, such as ground wheat for example.

In one embodiment the feed additive composition may be formulated as a premix. By way of example only the premix may comprise one or more feed components, such as one or more minerals and/or one or more vitamins.

In one embodiment at least one DFM and/or glycoside hydrolase such as an alpha-L-fucosidase (whether or not encapsulated) and/or at least one protease are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbate, glycerol, sucrose, propylene glycol, 1,3-propane diol, glucose, parabens, sodium chloride, citrate, acetate, phosphate, calcium, metabisulfite, formate and mixtures thereof.

In some embodiments, a glycoside hydrolase, such as an alpha-L-fucosidase, will be in a physiologically acceptable carrier. Suitable carriers may be large, slowly metabolised macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates. Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient. Once formulated, the compositions of the invention can be administered directly to the subject. The subjects to be treated can be animals. However, in one or more embodiments the compositions are adapted for administration to human subjects.

Non-limiting examples of compositions and methods disclosed herein include:

1. A method of preventing and/or treating an animal from having an intestinal pathogenic infection and/or diarrhea wherein the pathogenic infection and/or diarrhea is caused by a pathogen capable of binding to an animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site.

2. The method of embodiment 1 wherein the glycoside hydrolase is an alpha-L-fucosidase.

3. The method of embodiment 2 wherein the alpha-L-fucosidase is selected from the group consisting of glycoside hydrolase family 95 (GH95) and glycoside hydrolase family 29 (GH 29).

4. The method of embodiment 2 wherein the alpha-L-fucosidase is capable of removing a terminal alpha-1,2-linked fucose group from a glycan-containing structure either alone or in combination with an enzyme capable of (a) converting a blood group A antigen to a blood group H antigen or (b) converting a blood group B antigen to blood group H antigen.

5. The method of embodiment 1 wherein the pathogen is *Escherichia coli* expressing F18 fimbriae.

6. The method of embodiment 1 or 2 wherein the method further comprises administering to the animal an effective amount of a glycoside hydrolase or an alpha-L-fucosidase in combination with at least one direct fed microbial.

7. The method of embodiment 6 wherein the method further comprises administering to the animal an effective amount of a glycoside hydrolase or an alpha-L-fucosidase in combination with at least one direct fed microbial and at least one protease.

8. The method of any of embodiments 1, or 7 wherein the alpha-L-fucosidase is encapsulated.

9. The method of embodiment 6 wherein the alpha-L-fucosidase is encapsulated.

10. The method of any of embodiments 1 or 7 wherein the alpha-L-fucosidase and/or the direct fed microbial and/or the protease are administered in an animal feed or a premix.

11. The method of embodiment 6 wherein the alpha-L-fucosidase and/or the direct fed microbial and/or the protease are administered in an animal feed or a premix.

12. The method of any of embodiments 1 or 7 wherein the alpha-L-fucosidase is in the form of a granule.

11. The method of embodiment 6 wherein the alpha-L-fucosidase is in the form of a granule.

12. A composition for preventing and/or treating an animal having an intestinal pathogenic infection and/or diarrhea wherein the pathogenic infection is caused by a pathogen capable of binding to animal intestinal cell wherein said binding of the pathogen is dependent on the presence of a pathogen binding site having at least one glycan structure substituted with at least one alpha-1,2-L-fucose moiety comprising administering to the animal an effective amount of a glycoside hydrolase capable of removing the at least one alpha-1,2-L-fucose moiety from the pathogen binding site.

13. The composition of embodiment 12 wherein the glycoside hydrolase is an alpha-L-fucosidase.

14. The composition of embodiment 13 wherein the alpha-L-fucosidase is selected from the group consisting of glycoside hydrolase family 95 (GH95) and glycoside hydrolase family 29 (GH 29).

15. The composition of embodiment 13 wherein the alpha-L-fucosidase is capable of removing a terminal alpha-1,2-linked fucose group from a glycan-containing structure either alone or in combination with an enzyme capable of (a) converting a blood group A antigen to a blood group H antigen or (b) converting a blood group B antigen to blood group H antigen.

16. The method of embodiment 12 wherein the pathogen is *Escherichia coli* expressing F18 fimbriae.

17. The composition of embodiment 12 or 13 wherein said composition further comprises at least one direct fed microbial.

18. The composition of embodiment 17 wherein said composition further comprises at least one direct fed microbial and at least one protease.

19. The composition of any of embodiments 12 or 18 wherein the alpha-L-fucosidase is encapsulated.

20. The composition of embodiment 17 wherein the alpha-L-fucosidase is encapsulated.

21. The composition of any of embodiments 12 or 18 wherein the alpha-L-fucosidase and/or the direct fed microbial and/or the protease is administered to an animal as a feed or a premix.

22. The composition of embodiment 17 wherein the alpha-L-fucosidase and/or the at least one direct fed microbial and/or the at least one protease are administered to an animal as a feed or a premix.
23. The composition of any of embodiments 12 or 18 wherein the alpha-L-fucosidase is administered in a granule form.
24. The composition of embodiment 17 wherein the alpha-L-fucosidase is administered in a granule form.

EXAMPLES

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used with this disclosure.

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

General Methods

Standard recombinant DNA and molecular cloning techniques are well known in the art and are described by Sambrook, J. and Russell, D., *Molecular Cloning: A Laboratory Manual,* Third Edition, Cold Spring Harbor Laboratory Press, Cold Spring Harbor, N.Y. (2001); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et. al., *Short Protocols in Molecular Biology,* 5$^{th}$ Ed. Current Protocols and John Wiley and Sons, Inc., N.Y., 2002.

Example 1

Identification, Cloning and Expression of Fucosidases

Based on literature review, α-1,2-L-fucosidases are grouped in two glycosyl hydrolase (GH) families, GH29 and GH95 (the CaZy (Carbohydrate-Active EnZymes) classification). Protein sequences belonging to these two GH families were pulled out from the CaZy and NCBI databases, and phylogenetically analyzed using the software Mega 6. Several representative GH95 and GH29 fucosidases were selected with reference to their phylogenetic distribution and biological origin (fucosidases from probiotics were preferred) for expression. The list of fucosidases expressed is shown in Table 1.

TABLE 1

List of fucosidase enzymes expressed in this study

| Accession number | Unique ID | Taxonomy | Organism | Family |
| --- | --- | --- | --- | --- |
| WP_008767711 | CRC08377 | Bacteria | *Bacteroides thetaiotaomicron* | GH29 |
| WP_039972502 | CRC08378 | Bacteria | *Bacteroides pyogenes* | GH29 |
| WP_049703438 | CRC08379 | Bacteria | *Bacteroides* sp. | GH29 |
| WP_044155292 | CRC08380 | Bacteria | *Bacteroides intestinalis* | GH29 |
| WP_005799023 | CRC08381 | Bacteria | *Bacteroides fragilis* | GH29 |
| WP_005826218 | CRC08382 | Bacteria | *Bacteroides uniformis* | GH29 |
| AIF89911 | CRC08390 | Bacteria | *Bifidobacterium longum* | GH95 |
| ACJ53393 | CRC08391 | Bacteria | *Bifidobacterium longum* | GH95 |
| AAQ72464 | CRC08392 | Bacteria | *Bifidobacterium bifidum* | GH95 |
| ADV44858 | CRC08394 | Bacteria | *Bacteriodes helcogenes* | GH95 |
| ALJ60603 | CRC08396 | Bacteria | *Bacteriodes cellulosilyticus* | GH95 |
| ACD04030 | CRC08400 | Bacteria | *Akkermansia muciniphila* ATCC BAA-83 | GH95 |
| AKA50945 | CRC08401 | Bacteria | *Bacteroides fragilis* | GH95 |
| EFC70146 | CRC08505 | Bacteria | *Prevotella* sp. | GH95 |
| EWY82402 | CRC08370 | Fungi | *Fusarium oxysporum* | GH29 |

A. Cloning and Expression of Bacterial Fucosidases in *Bacillus subtilis*

Figure 1B:
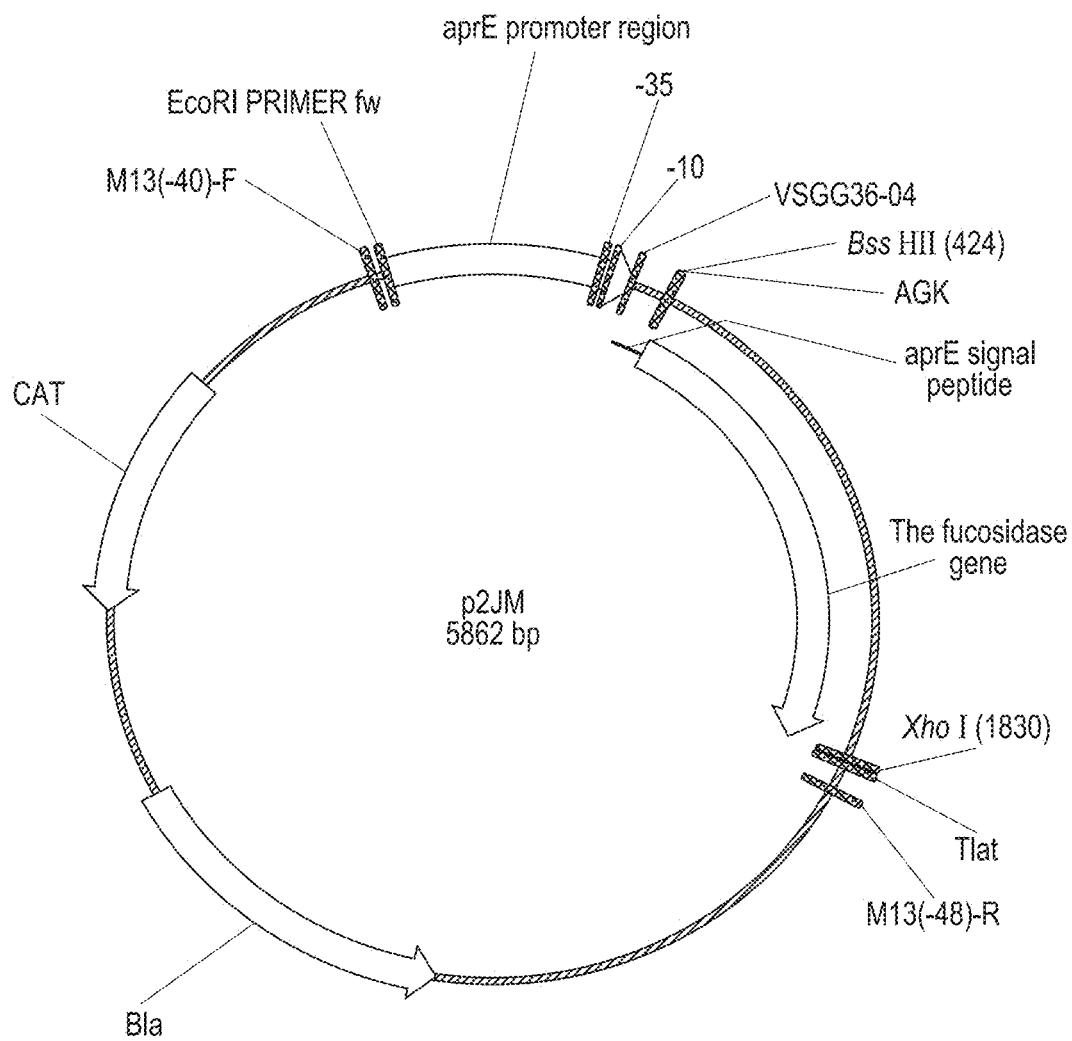
FIG. 1B depicts an exemplary plasmid map of p2JM.

Synthetic genes encoding mature bacterial fucosidase sequences were codon optimized and synthesized by GeneRay (Shanghai, China). The synthesized genes were inserted into the p2JM and p3JM vectors (Vogtentanz (2007) Protein Expr. Purif, 55:40-52). Genes cloned into both vectors are under the control of an aprE promoter, with a difference in that the p2JM vector also contains an aprE signal sequence which was used to direct target protein secretion in *B. subtilis*, and an oligonucleotide named AGK-proAprE that encodes peptide Ala-Gly-Lys to facilitate the secretion of the target protein. For genes inserted into the p3JM vectors, the start codon and the gene sequence encoding the mature protein was placed right after the aprE promoter. Exemplary plasmid maps are shown in FIGS. 1A and 1B.

The plasmids were amplified using Illustra TempliPhi 100 Amplification Kit (GE Healthcare Life Sciences, NJ). A suitable *B. subtilis* strain was transformed with the amplification product using a method known in the art (WO 01/14490). The *B. Subtilis* transformants were selected on Luria Agar plates supplemented with 5 ppm Chloramphenicol. The colonies from the transformation plates were inoculated into 5 ml LB medium and incubated at 37° C. overnight. Selective growth of *B. Subtilis* transformants harboring the plasmids was performed at 37° C. for 40 hours in MBD medium (enriched semi-defined medium based on MOPs buffer, with urea as major nitrogen source, glucose as the main carbon source, and supplemented with 4% soytone for rebust cell growth) containing 5 ppm chloramphenicol. Cells were harvested by centrifugation, and both cells and supernatants were analyzed by SDS-PAGE. Bacterial fucosidase expression was confirmed with visible protein bands on SDS-PAGE gels.

B. Cloning and Expression of Selected Fucosidases in *Trichoderma reesei*

Figure 2:
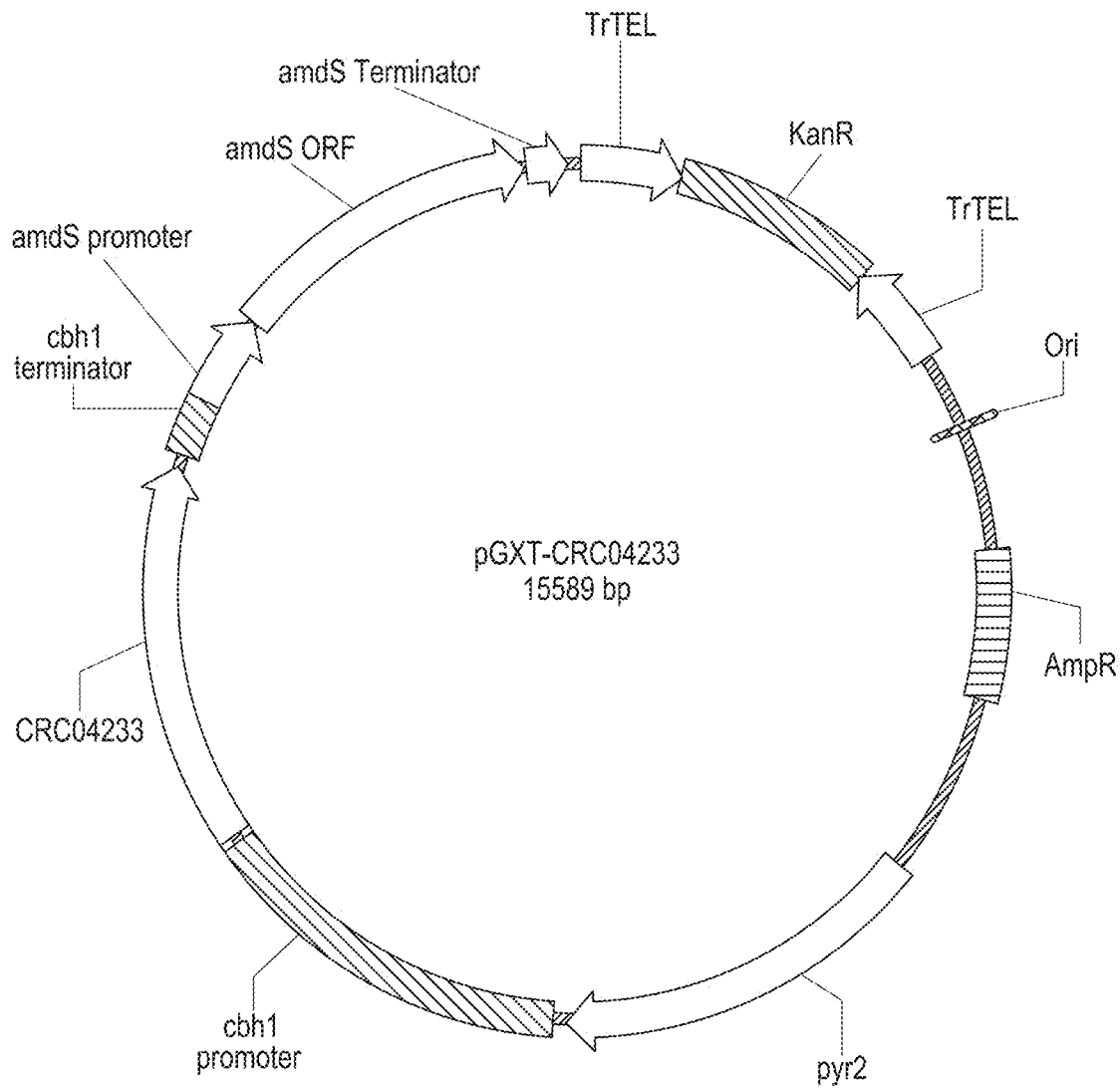
FIG. 2 depicts an exemplary plasmid map of pGXT-GOI.

Fungal fucosidase genes were codon optimized based on predicted protein sequences and synthesized by GeneRay (Shanghai, China). Both synthesized and amplified genes were inserted into pGXT vectors (the same as the pTTTpyr2 vector as described in published PCT Application WO2015/017256). Genes cloned in pGXT vector are under the control of CBH1 promotor and the native signal peptide are used for expression. Exemplary plasmid map is shown in FIG. 2.

A suitable *Trichoderma reesei* strain was transformed with the expression plasmids (method described in published PCT application WO 05/001036) using protoplast transformation (Te'o et al. (2002) J. Microbiol. Methods 51:393-99). Transformants were selected on a medium containing acetamide as a sole source of nitrogen. After 5 days of growth on acetamide plates, transformants were collected and subjected to fermentation in 250 mL shake flasks in defined media containing a mixture of glucose and sophorose. The supernatant of the fermentation broth was collected by filtration and was subject to SDS-PAGE for expression. Fungal fucosidase expression was confirmed with visible protein bands on SDS-PAGE gels.

Example 2

Biochemical Characterization of Fucosidases Using Fucosyllactose Substrate

1. Assay for α-1,2-Fucosidase Activity in Crude Culture Supernatants

Figure 3:
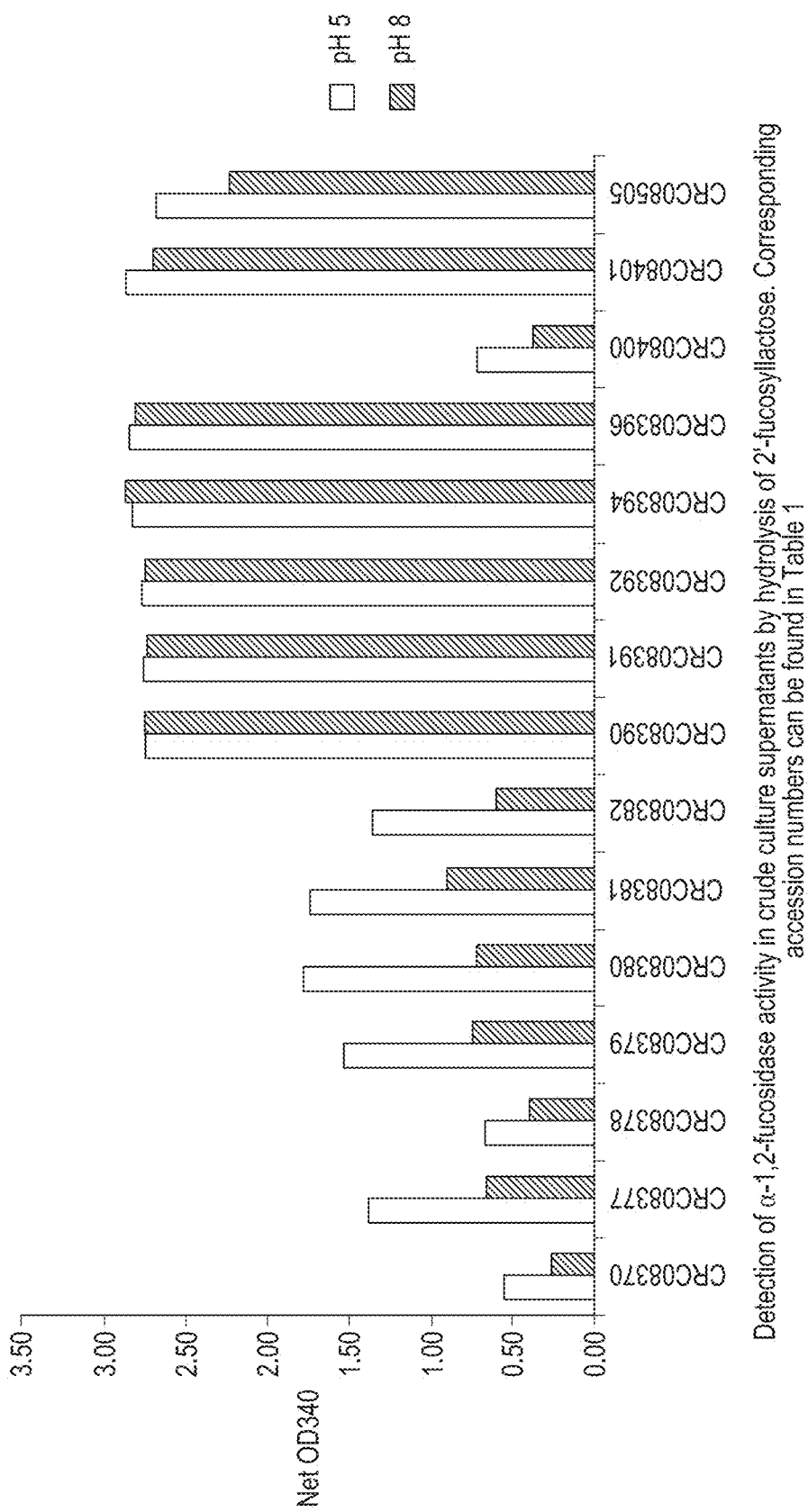
FIG. 3 is graph of alpha-1,2-fucosidase activity in crude culture supernatants by hydrolysis of 2'-fucosyllactose.

To identify active α-1,2-fucosidases, crude culture supernatants of expressed bacterial and fungal fucosidases were assayed at 37° C. using 10 mM 2'-fucosyllactose as substrate. Reaction was initiated by adding 5 µL crude sample to 45 µL substrate solution in 50 mM sodium acetate buffer (pH 5.0) and 50 mM NaOH-HEPES buffer (pH 8.2), respectively. Crude sample with no enzyme expressed was assayed under the same conditions as a blank control. After 10 min, released L-fucose was detected using K-fucose kit (Megazyme, Ireland). The fucosidase activity observed, measured as absorbance at 340 nm (enzyme blank subtracted) is reported in FIG. 3.

2. Measurement of Specific α-1,2-Fucosidase Activity

Several expressed fucosidases were purified for further characterization. Specific activity of purified fucosidases was measured with 10 mM 2'-fucosyllactose. Prior to reaction, enzyme solution was prepared by six rounds of 2-fold serial dilution starting from an appropriate dose (e.g. 5 ppm). Reaction was initiated by adding 5 µL of diluted enzyme sample or water (blank control) to 45 µL substrate solution in 50 mM sodium phosphate buffer (pH 6.8), followed by incubation at 37° C. for 10 min. Released L-fucose was detected using K-fucose kit. Dose response curves were generated with absorbance changes as Y values and enzyme doses as X values, and linear part of the curves was used for calculation of specific activity of the purified enzyme samples. One unit of α-1,2-fucosidase activity was defined as the amount of enzyme that can catalyze release of one µmole L-fucose per minute under the described assayed conditions. Specific α-1,2-fucosidase activity of all the fucosidases was given in Table 2. It was observed, that under these conditions, the bacterial α-1,2-fucosidases from GH95 family displayed higher specific activity than the other enzymes.

TABLE 2

Specific activity of α-1,2-fucosidases measured using 2'-fucosyllactose as substrate.

| Unique ID | Organism | Specific activity (U/mg) |
| --- | --- | --- |
| CRC08377 | *Bacteroides thetaiotaomicron* | 26 |
| CRC08378 | *Bacteroides pyogenes* | 22 |
| CRC08379 | *Bacteroides* sp. | 27 |
| CRC08380 | *Bacteroides intestinalis* | 39 |
| CRC08381 | *Bacteroides fragilis* | 44 |
| CRC08382 | *Bacteroides uniformis* | 32 |
| CRC08390 | *Bifidobacterium longum* | 475 |
| CRC08391 | *Bifidobacterium longum* | 593 |
| CRC08392 | *Bifidobacterium bifidum* | 421 |
| CRC08394 | *Bacteriodes helcogenes* | 107 |
| CRC08396 | *Bacteriodes cellulosilyticus* | 1306 |
| CRC08400 | *Akkermansia muciniphila* ATCC BAA-835 | 40 |
| CRC08401 | *Bacteroides fragilis* | 670 |
| CRC08505 | *Prevotella* sp. | 226 |
| CRC08370 | *Fusarium oxysporum* | 4 |

Example 3 pH and Temperature Profile for Various Fucosidases

Figure 4:
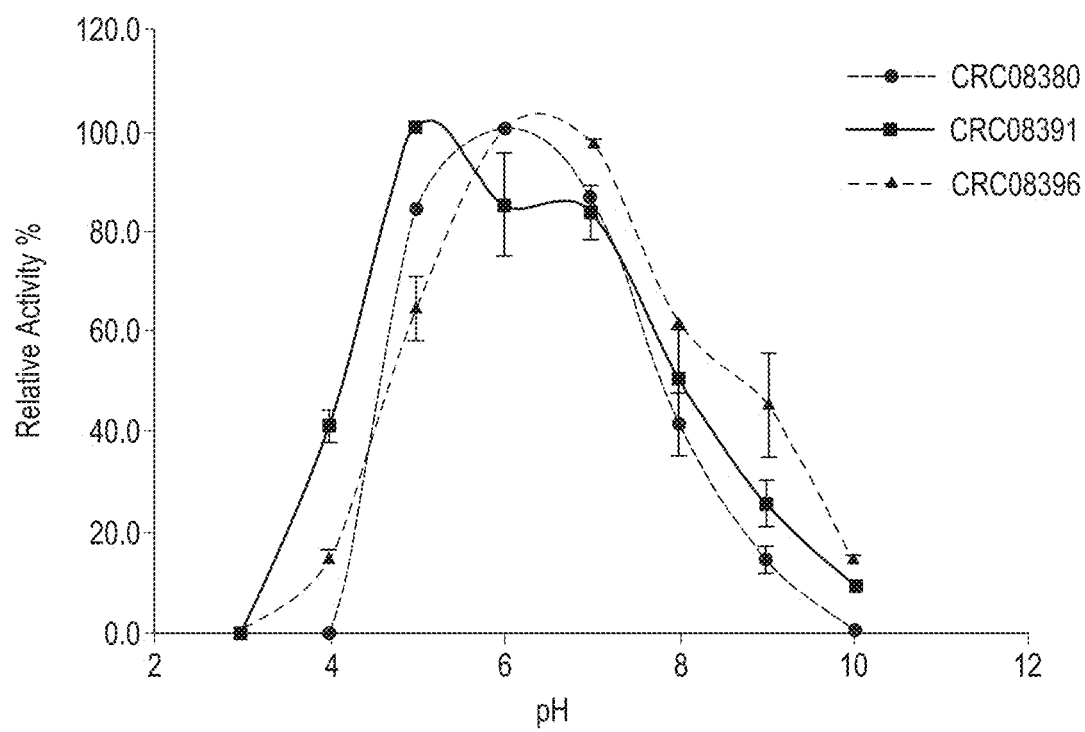
FIG. 4 is a graph of pH effect on fucosidase activity towards 2'fucosyllactose.
Figure 5:
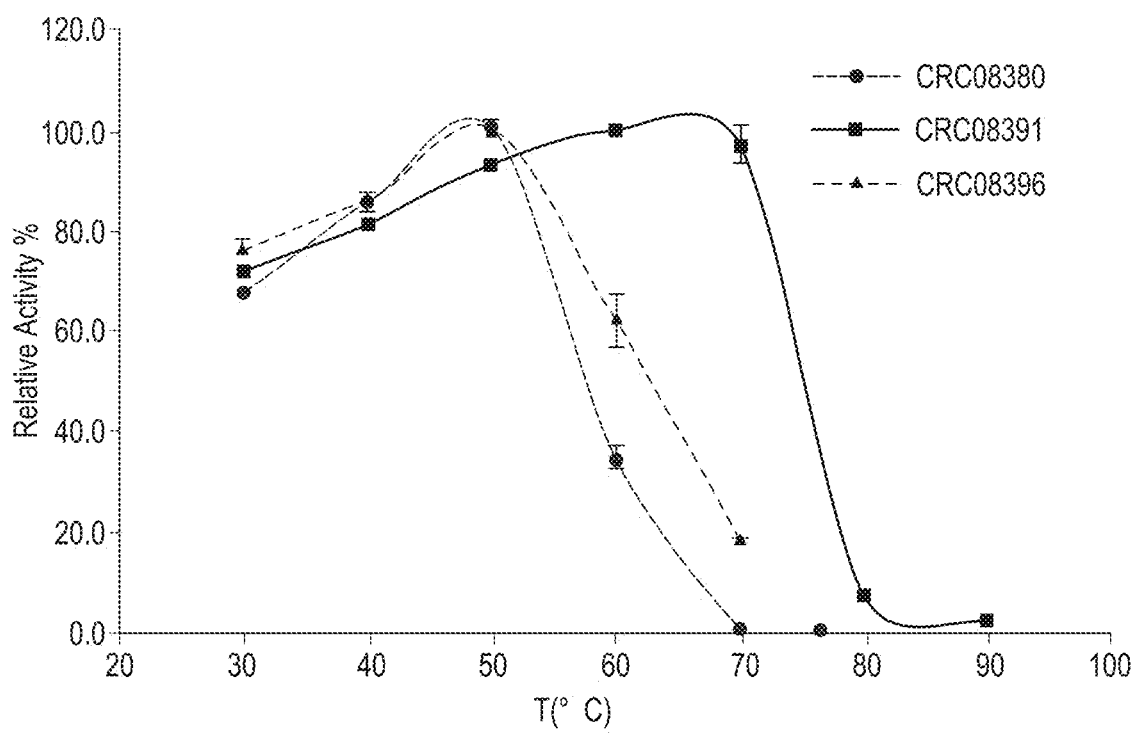
FIG. 5 is a graph of temperature effect on fucosidase activity towards 2'fucosyllactose.

Fucosidases were assayed to determine their pH and temperature profiles. To determine optimum pH, the ability of α-1,2-fucosidase candidates to hydrolyze 2'-fucosyllactose at 37° C. was measured in 50 mM sodium acetate/HEPES/Glycine buffer with pH ranging from 3.0 to 10.0. To determine optimum temperature, the ability of the fucosidase candidates to hydrolyze 2'-fucosyllactose in 50 mM sodium phosphate buffer was measured at 10° intervals between 30° C. and 90° C. All reactions were performed in duplicates and were carried out for 10 min. The results are shown in FIGS. 4, 5 and Table 3.

TABLE 3 pH and Temperature ranges and optima of select α-1,2-fucosidases

| Fucosidase | pH range | pH optima | T range | T optima |
| --- | --- | --- | --- | --- |
| CRC08380 | 4.8-6.8 | 6.0 | 32-55 | 50 |
| CRC08391 | 4.5-7.4 | 5.0 | 30-73 | 60 |
| CRC08396 | 5.2-7.7 | 6.0-7.0 | <30-58 | 50 |

Example 4

Evaluation of Fucosidases Activity at Low pH and in Presence of Pepsin

Figure 6A:
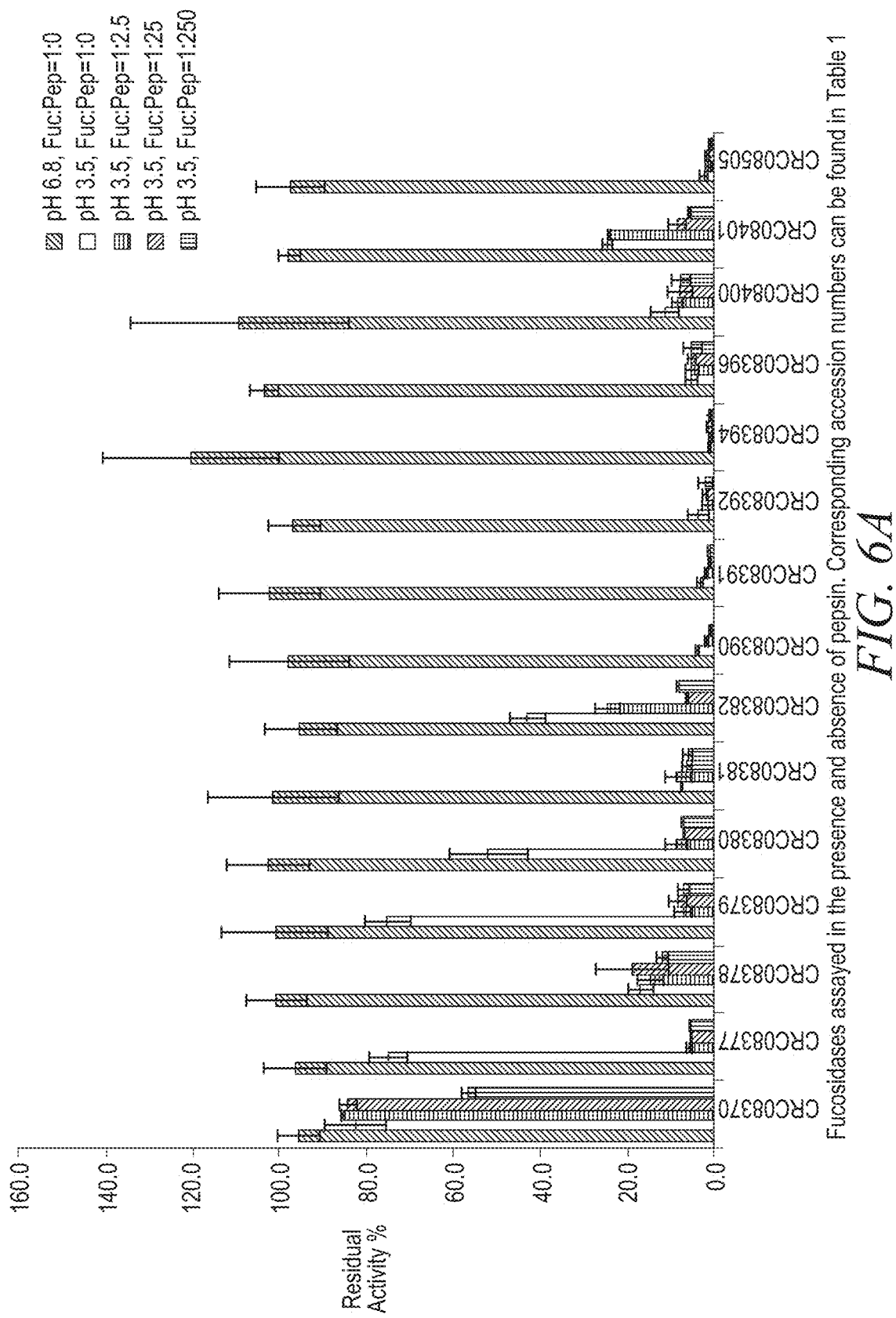
FIG. 6A is a graph of fucosidases assayed in the presence and absence of pepsin.
Figure 6B:
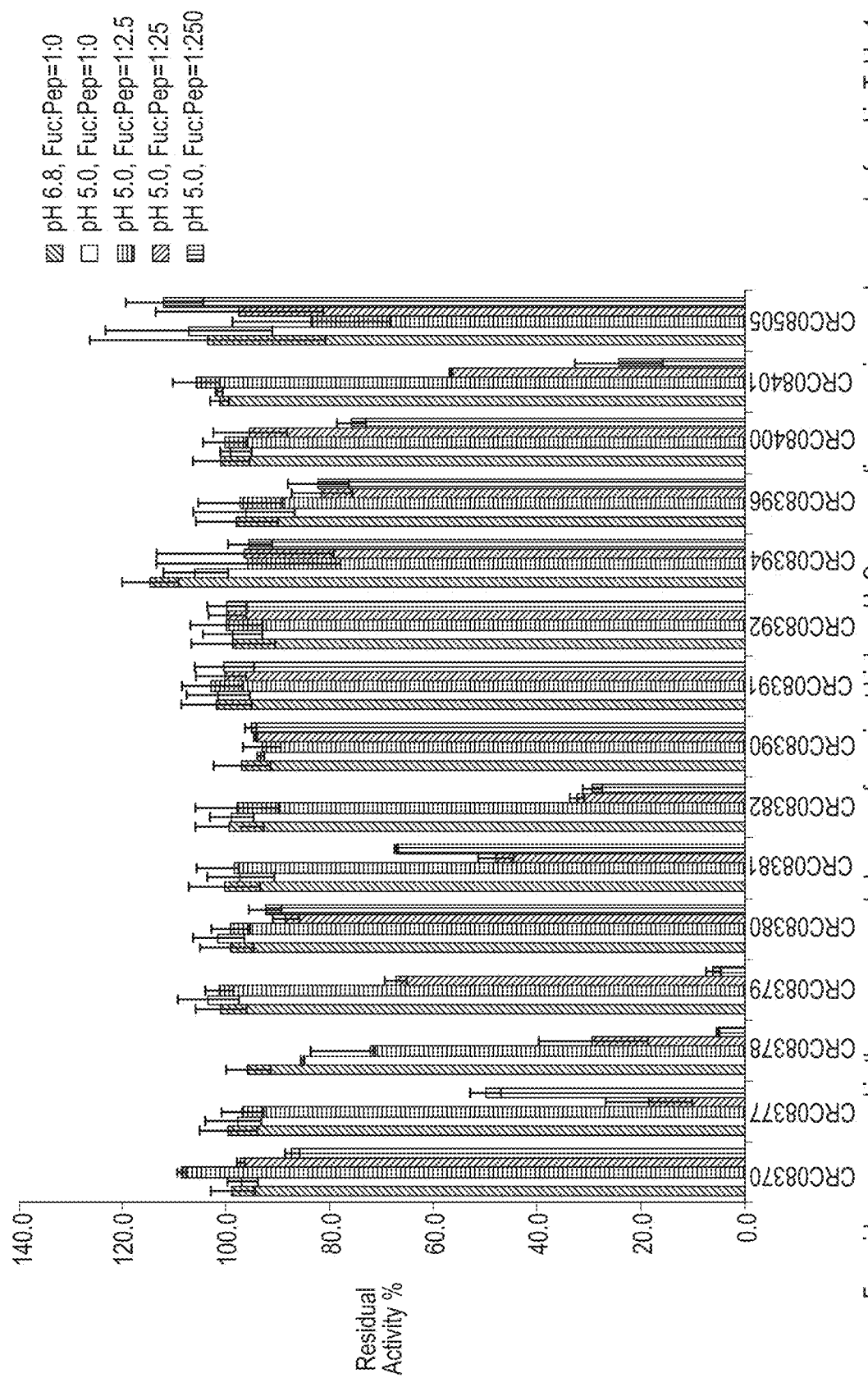
FIG. 6B is a graph of fucosidases assayed in the presence and absence of pepsin.

To evaluate fucosidase activity at low pH and pepsin resistance of α-1,2-fucosidase candidates, enzyme samples were incubated with pepsin (Sigma, Cat. No. P7000) in 50 mM Glycine-HCl buffer (pH 3.5) and 50 mM sodium acetate buffer (pH 5.0), respectively. 100 ppm fucosidase was mixed with pepsin at ratios of 1:0, 1:2.5, 1:25, and 1:250 and enzyme mixtures were incubated at 37° C. Meanwhile, 100 ppm fucosidase was incubated alone in 50 mM sodium phosphate buffer (pH 6.8) at 37° C. and 4° C. (as control). Following 30-min incubation, enzyme samples were diluted to an appropriate dose and subsequently assayed with 2'-fucosyllactose at 37° C. in 50 mM sodium phosphate buffer (pH 6.8). purified water was assayed under the same conditions as a blank control. Residual α-1,2-fucosidase activity was calculated as 100×Net OD340(incubated enzyme)/Net OD340(enzyme stored at 4° C.). All reactions were done as duplicates. The results illustrated in FIGS. 6A and 6B show that bacterial α-1,2-fucosidases were intolerant to the acidic condition (pH 3.5) of this assay, but were stable under less acidic conditions (pH 5.0).

Example 5

Evaluation of Fucosidase Activity on Various Natural Substrates

Figure 7:
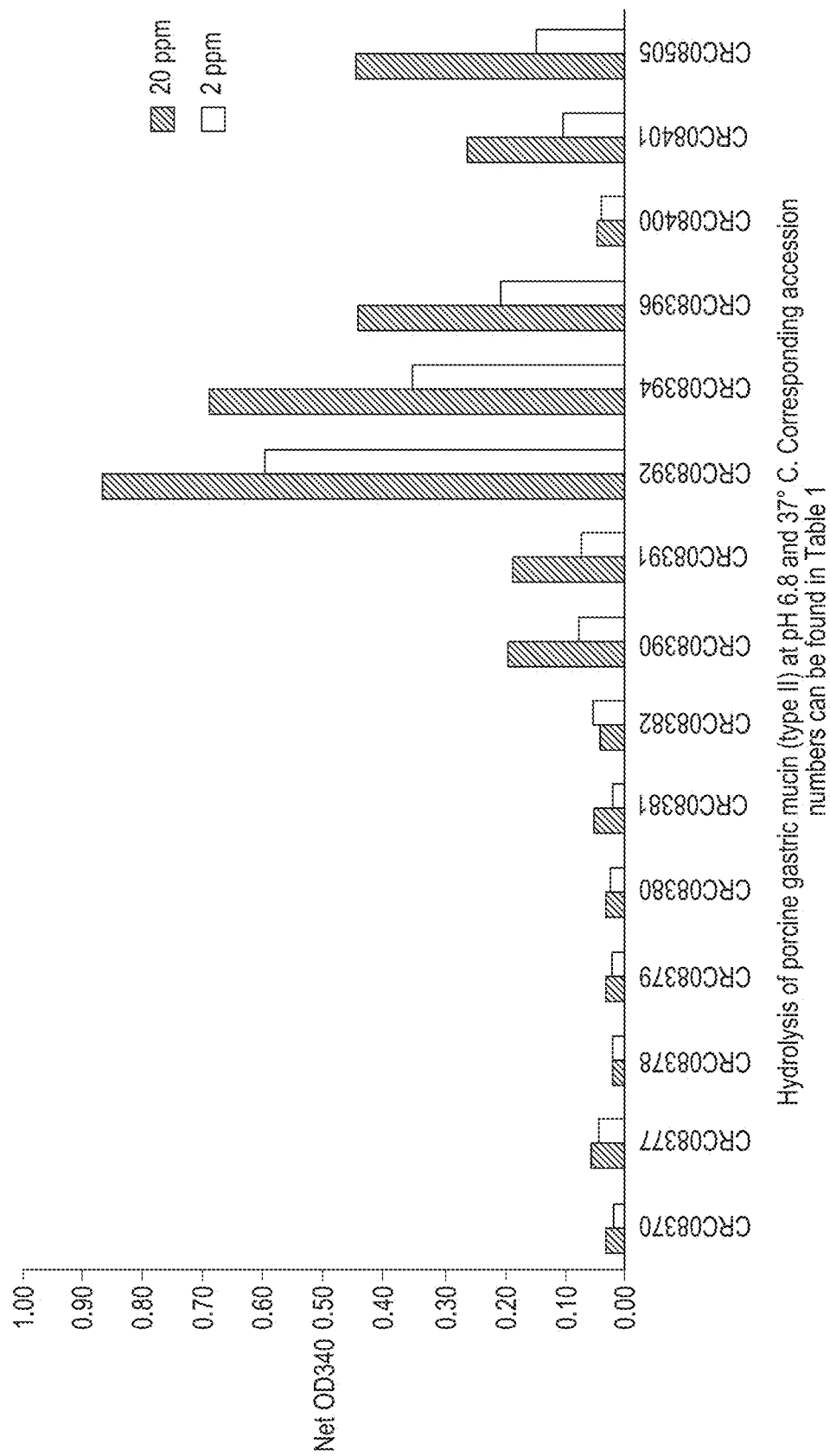
FIG. 7 is a graph of the hydrolysis of porcine gastric mucin (type II) at pH 6.8 and 37° C.
Figure 8:
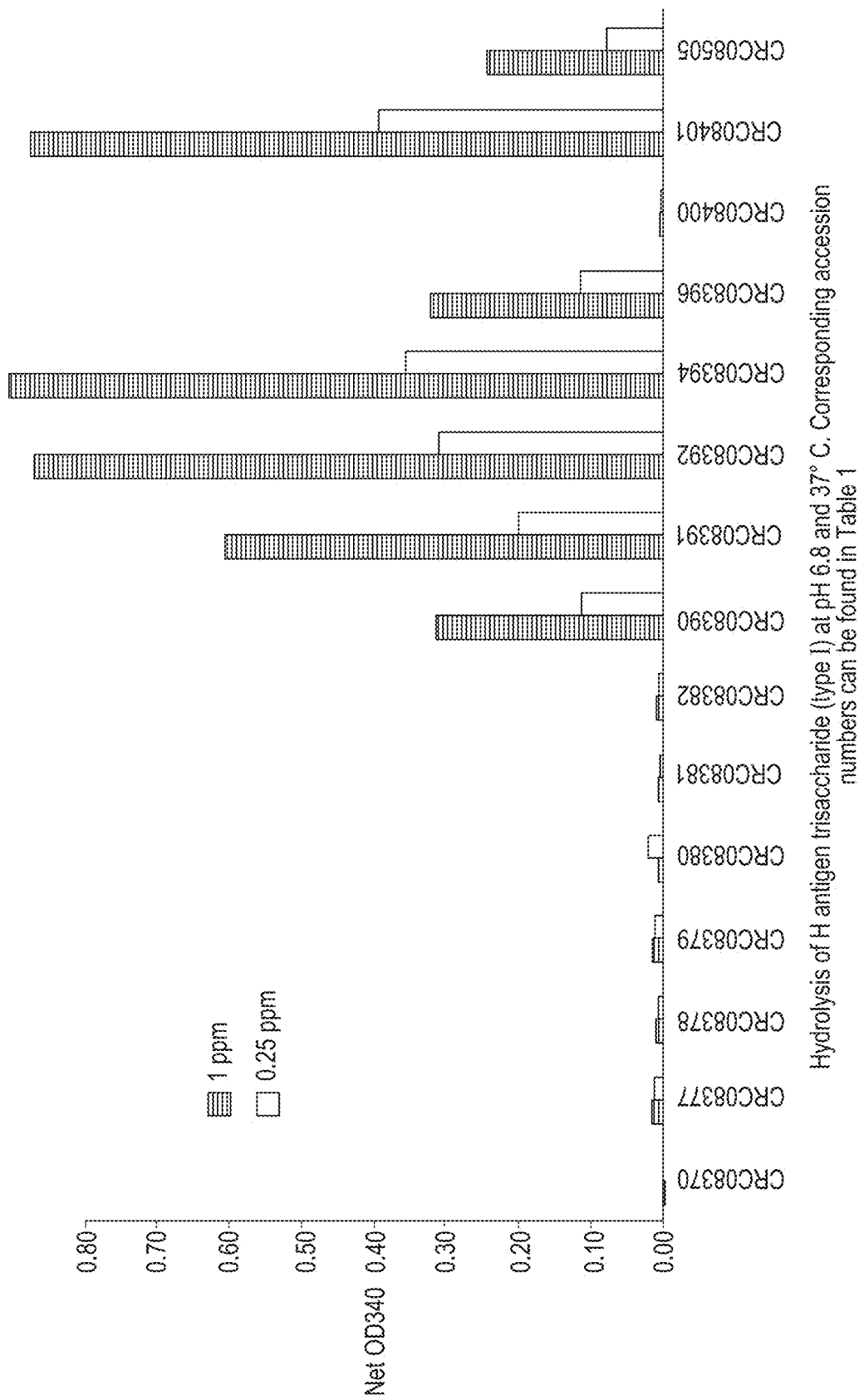
FIG. 8 is a graph of the hydrolysis of H antigen trisaccharide (type I) at pH 6.8 and 37° C.

The hydrolysis activity of α-1,2-fucosidase candidates was assessed towards porcine gastric mucin (type II) and H antigen triasaccharide (type I). Hydrolysis of 40 mg/mL porcine gastric mucin (type II) was assayed using 2 and 20 ppm of enzyme samples while hydrolysis of 3 mM H antigen triasaccharide (type I) was assayed using 0.25 ppm and 1 ppm of enzyme samples. Both reactions were carried out for 10 minutes using assay conditions described in Section 2 of Example 4. All reactions were carried out at 37° C. in 50 mM sodium phosphate buffer (pH 6.8). purified water was assayed under the same conditions as a blank control. Illustrated in FIGS. 7 and 8 bacterial α-1,2-fucosidases from GH95 family, except CRC08400, displayed higher hydrolysis activity towards both mucin and H antigen triasaccharide (type I). Specifically, CRC08392 exhibited the highest activity on mucin degradation (Table 4), while CRC08394 and CRC08401 were most active in hydrolyzing H antigen triasaccharide (type I). (FIG. 8).

TABLE 4

Specific hydrolysis activity of α-1,2-fucosidases with porcine gastric mucin (type II) as substrate.

| Fucosidase | Specific activity (U/mg) |
|---|---|
| CRC08392 | 459 |
| CRC08394 | 120 |
| CRC08396 | 40 |
| CRC08401 | 21 |
| CRC08505 | 29 |

Example 6

Effect of Fucosidases on Adhesion of F18+ ETEC Strain to Intestinal Cell Culture In Vitro Neonatal porcine jejunum derived IPEC-1 (ACC-705; DSMZ, Braunschweig, Germany) cells are seeded in 96-well plates (NUNC) and allowed to attach for 16 hours. Control wells receive only culture medium without cells and serve as control. Fucosidases are diluted in Buffer 1 (12.5 mM HEPES, 141 mM NaCl, 0.5 mM MgCl2, 0.15 mM CaCl2, 0.1% gelatin, pH 6) and added to the 96-well plate containing the IPEC-1 cells or medium alone at a final concentration of 2, 20, or 200 ppm in a total volume of 100 μL. The plate is incubated at 37° C. for 30 minutes. Following incubation, the plate is washed with 100 μL of Buffer 2 (12.5 mM HEPES, 141 mM NaCl, 0.5 mM MgCl2, 0.15 mM CaCl2, 0.1% gelatin, pH 7.4). The adhesion of F18 ETEC to IPEC-1 cells is measured essentially as described in Hedegaard C J, Strube M L, Hansen M B, Lindved B K, Lihme A, Boye M, et al. (2016). Natural Pig Plasma Immunoglobulins Have Anti-Bacterial Effects: Potential for Use as Feed Supplement for Treatment of Intestinal Infections in Pigs. PLoS ONE 11(1): e0147373, with the exception that in the present experiments F18+ ETEC strain is used, without incubation with immunoglobulins.

Example 7

Effect of Fucosidases on Reduced F18 ETEC Colonization In Vivo

A. Preparation of Controlled Release Fucosidases Granules

Controlled release fucosidase granules are prepared using the formula in Table 5 below. Into a Vector FL-1 fluid bed coater, 670 grams of sodium sulfate crystals (Minera Santa Marta, Spain), sieved to between 150 and 355 microns, are added as granule cores. The cores are fluidized at an inlet temperature of 70 degrees C., and a fluidization airflow of 50 cfm.

An enzyme solution is prepared consisting of 400 grams of a 25% w/w fucosidase enzyme ultrafiltration concentrate well mixed together with 250 grams of a 16% w/w aqueous solution of Erkol 5-88 (Erkol Corporation, Guardo, Spain) partially hydrolyzed polyvinyl alcohol. The enzyme-PVA solution, designated "SP1" is sprayed onto the fluidized cores at an atomization pressure of 20 psi and a spray rate of 7 grams per minute, increasing to 12 grams per minute after 30 minutes, maintaining the 70 degrees C. inlet temperature. A PVA/talc solution (SP2) is prepared by combining 250 grams of 15% w/w PVA solution with 200 grams of a 30% talc suspension. The PVA/talc mixture is sprayed onto the enzyme coated cores at a rate of 10 g/min, maintaining the above inlet temperature and atomization pressure. Two kilograms of a 25% w/w sodium sulfate solution (SP3) are sprayed onto the PVA/talc-coated cores at a spray rate of 15 g/min, maintaining the above inlet temperature and atomization pressure. Finally, a controlled release coated (SP4) is prepared by combining 1200 grams of a 30% w/w EUDRAGIT® L 30 D-55 (methacrylate cationic synthetic polymer) latex suspension (Evonik Corporation, Kennesaw, Georgia) with 800 grams of a 30% w/w suspension of talc, maintaining the above inlet temperature and atomization pressure. temperature and atomization pressure. From the Vector FL-1 coater, 2000 grams of controlled release fucosidase granules are harvested.

TABLE 5

Preparation of Controlled Release fucosidases granules

| Layer | Component | Solution (g) | Solution % w/w | Solids (g) | Granule % w/w |
|---|---|---|---|---|---|
| core | sodium sulfate | 670 | 100% | 670 | 33.5% |
| SP1 | fucosidase | 400 | 25% | 100 | 5.0% |
| SP1 | PVA | 250 | 16% | 40 | 2.0% |
| SP2 | PVA | 200 | 15% | 30 | 1.5% |
| SP2 | talc | 200 | 30% | 60 | 3.0% |
| SP3 | sodium sulfate | 2000 | 25% | 500 | 25.0% |
| SP4 | Eudragit L 30 D-55 | 1200 | 30% | 360 | 18.0% |
| SP4 | talc | 800 | 30% | 240 | 12.0% |
| TOTAL | | | | 2000 | 100.0% |

B. Effect of Fucosidase Diet on Reduced F18 ETEC Colonization

The controlled release fucosidase granules of Example 7 section A are combined with a corn soy feed at a dose of 1,000 grams per ton. The granules are fed to weaning piglets. The controlled release coating prevents the fucosidase from being released during transit through the stomach (at approximately pH 3) but releases the fucosidase enzyme into the intestinal tract of the piglets, where the fucosidase is removing alpha 1,2 fucose groups from glycans; thereby, significantly reducing the potential for colonization of the gut by enterotoxic F18 *E. coli* and associated diarrhea.

Example 8

Evaluation of Fucosidase Induced Release of Fucose from Tissue Samples from the Small Intestine (Duodenum)

Approximately a 1 cm$^2$ tissue sample was obtained from the duodenum from two different 24 day old piglets with unknown blood-type (piglet_1 and piglet_2). These tissue samples were placed in a 12 ml tube and covered with 3 ml of assay-buffer (Assay-buffer: 50 mM sodium phosphate buffer pH 6+137 mM NaCl, 2.7 mM KCl) either with or without 100 ppm fucosidase CRC08392. (See Table 1 for corresponding accession number.) The samples were incubated at 37° C. for 1 hour One aliquot was removed then rest of the samples remained in the incubator. The samples were spun down with a table centrifuge. Supernatants were transferred to a centrifugal filter device (with a 10 kDA cut off), centrifuged for ~1 hour. The released fucose was quantified using the L-Fucose kit from Megazyme according to the manufacturer's instructions for the Micro plate assay procedure.

Figure 11:
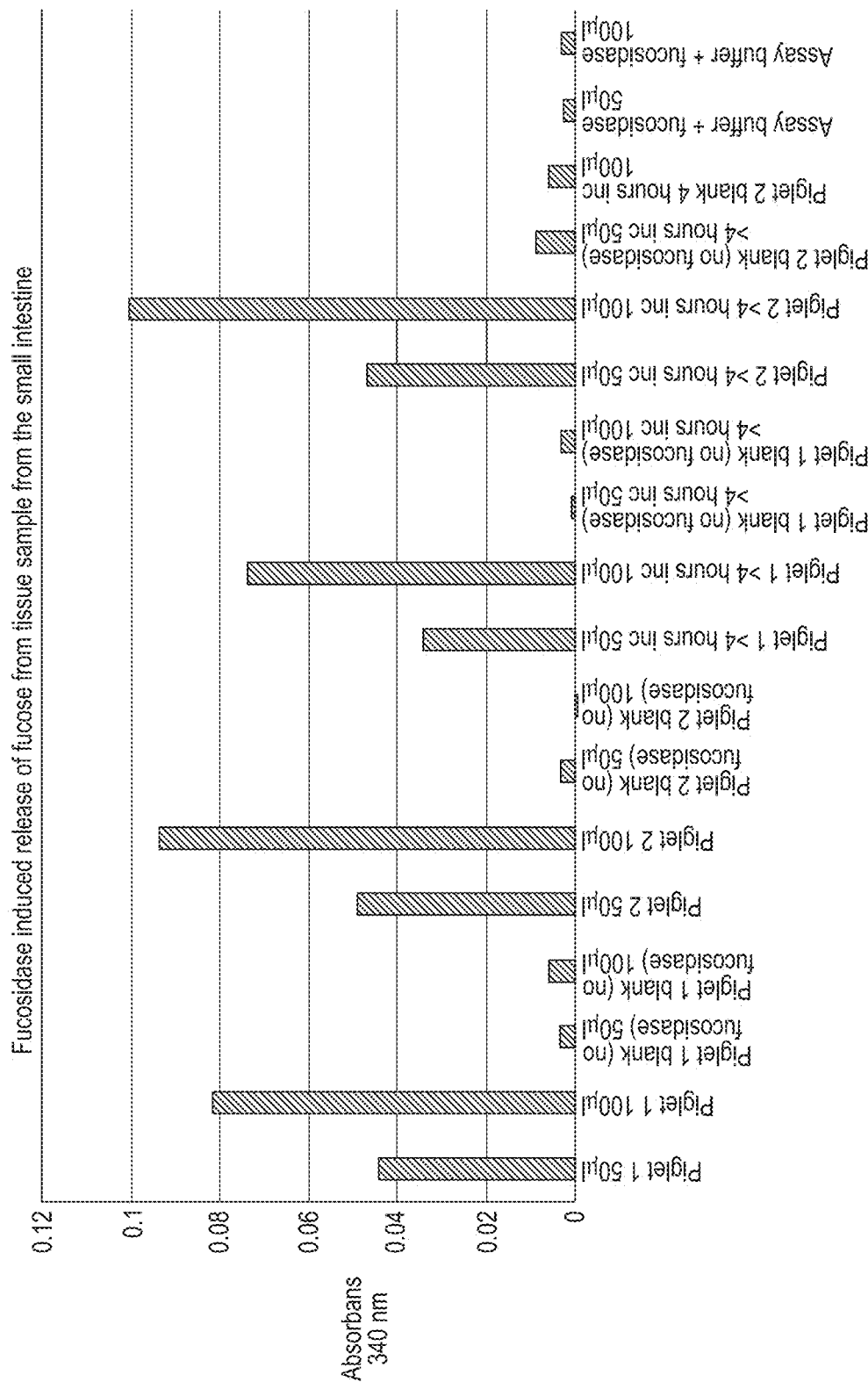
FIG. 11 depicts the fucosidase induced release of fucose from tissue sample from the small intestine of a piglet.

The results depicted in FIG. 11 show that fucose was released from the tissue sample using fucosidase (CRC08392 having Accession No. AAQ72464 (Table 1)). It appears that these in vitro results may correlate to the results expected if this fucosidase was used in vivo.

What is claimed is:

1. A method of treating an animal with an intestinal pathogenic infection and/or diarrhea wherein the pathogenic infection and/or diarrhea is caused by a pathogen capable of binding to an animal intestinal cell wherein said binding of the pathogen is dependent on the presence of a pathogen binding site having at least one glycan structure substituted with at least one alpha-1,2-L-fucose moiety comprising administering to the animal an effective amount of a purified glycoside hydrolase family 95 (GH95) alpha-L-fucosidase capable of removing the at least one alpha-1,2-L-fucose moiety from the pathogen binding site.

2. The method of claim 1 wherein the GH95 alpha-L-fucosidase is capable of removing a terminal alpha-1,2-linked fucose group from a glycan-containing structure.

3. The method of claim 1 wherein the pathogen is *Escherichia coli* expressing F18 fimbriae.

4. The method of claim 1 wherein the method further comprises administering to the animal an effective amount of a GH95 alpha-L-fucosidase in combination with at least one direct fed microbial.

5. The method of claim 4 wherein the method further comprises administering to the animal an effective amount a GH95 alpha-L-fucosidase in combination with at least one direct fed microbial and at least one protease.

6. The method of claim 5 wherein the GH95 alpha-L-fucosidase and/or the direct fed microbial and/or the protease are administered in an animal feed or a premix.

7. The method of claim 4 wherein the GH95 alpha-L-fucosidase is encapsulated.

8. The method of claim 4 wherein the GH95 alpha-L-fucosidase and/or the direct fed microbial are administered in an animal feed or a premix.

9. The method of claim 4 wherein the GH95 alpha-L-fucosidase is in the form of a granule.

10. The method of claim 1 wherein the GH95 alpha-L-fucosidase is encapsulated.

11. The method of claim 1 wherein the GH95 alpha-L-fucosidase is in the form of a granule.

12. The method of claim 1, wherein the GH95 alpha-L-fucosidase is derived from *Bifidobacterium bifidum, Bifidobacterium longum, Bacteroides fragilis*, or *Bacteroides helcogenes*.

13. The method of claim 1, further comprising administering an enzyme capable of (a) converting a blood group A antigen to a blood group H antigen or (b) converting a blood group B antigen to blood group H antigen.

14. The method of claim 13, wherein the enzyme capable of converting a blood group A antigen to a blood group H antigen is an alpha-N-acetylgalactosidase.

15. The method of claim 13, wherein the enzyme capable of converting a blood group B antigen to blood group H antigen is an alpha-galactosidase.

* * * * *